United States Patent [19]

Dolle, III et al.

[11] Patent Number: 5,976,894
[45] Date of Patent: Nov. 2, 1999

[54] COMBINATORIAL AMIDE ALCOHOL LIBRARIES

[75] Inventors: Roland Ellwood Dolle, III, King of Prussia, Pa.; Timothee Felix Herpin, Princeton, N.J.; Yvonne Class Shimshock, Somerville, N.J.; Cullen Lee Cavallaro, Highstown, N.J.

[73] Assignee: Pharmacopeia, Inc., Princeton, N.J.

[21] Appl. No.: 08/843,214

[22] Filed: Apr. 14, 1997

[51] Int. Cl.$^6$ ............... G01N 33/566; G01N 33/543; G01N 33/53

[52] U.S. Cl. ............... 436/501; 436/518; 435/7.1; 564/201

[58] Field of Search ............... 435/7.1; 436/518, 436/501; 554/61

[56] References Cited

U.S. PATENT DOCUMENTS 5,565,324 10/1996 Still et al. .................. 435/6
5,712,171 1/1998 Zambias et al. ............. 436/518

FOREIGN PATENT DOCUMENTS

WO93/06121 4/1993 WIPO .

OTHER PUBLICATIONS

Rotella "Solid Phase Synthesis of Olefin and Hydroxyethylene Peptidomimetics" *J. Am. Chem. Soc.* 118, 12246–12247 (1996).

Murphy et al. "Combinatorial Organic Synthesis of Highly Functionalized . . . " *J. Am. Chem. Soc.* 117, 7029–7030 (1995).

Baldwin et al. "Synthesis of a Small Molecule Combinatorial Library Encoded . . . " *J. Am. Chem. Soc.* 117, 5588–5589 (1995).

Wang et al. "Synthetic Chemical Diversity: Solid Phase Synthesis of Libraries . . . " *J. Med. Chem.* 38, 2995–3002 (1995).

Kick et al. "Expedient Method for the Solid–Phase Synthesis of Aspartic Acid . . . " *J. Med. Chem.* 38, 1427–1430 (1995).

Gordon et al. "Applications of Combinatorial Technologies to Drug Discovery . . . " *J. Med. Chem.* 37, 1385–1401 (1994).

*Primary Examiner*—Ponnathapura Achutamurthy
*Assistant Examiner*—Joseph W. Ricigliano
*Attorney, Agent, or Firm*—Heslin & Rothenberg, P.C.

[57] ABSTRACT

Combinatorial chemical libraries of the Formula [S]-C(O)-L'-Z containing dihyroxy amides and hydroxyphosphonate amides are disclosed, in which [S] represents a solid support and -L'-Z is a linker/ligand residue. In these libraries, Z is

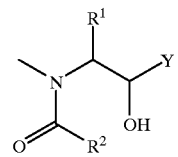

and Y is $-P(O)(OR^6)(OR^7)$, $-CH(OH)-COR^8$, $-CH_2CH=CH_2-CH_2CH(OH)CH_2OH$, $-CH_2CHO$, $-CH_2CH_2OH$, $-CH_2CH_2OC(O)NHR^{26}$, $-CH_2CH_2NR^{27}R^{28}$, or

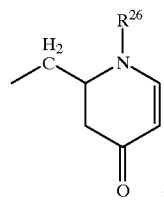

The combinatorial libraries are optionally encoded with tags. The use of these libraries in assays to discover biologically active compounds is also disclosed.

19 Claims, No Drawings

COMBINATORIAL AMIDE ALCOHOL LIBRARIES

TECHNICAL FIELD

This invention relates generally to the synthesis of chemical compounds, and more particularly, to the synthesis of combinatorial libraries of amide alcohols.

BACKGROUND OF THE INVENTION

Methods for the synthesis of large numbers of diverse compounds which can be screened for various possible physiological or other activities are of interest (Ellman, et. al. *Chem. Rev.* 96: 555–600 (1996)). Techniques have been developed in which individual units are added sequentially as part of the chemical synthesis to produce all or a substantial number of the possible compounds which can result from all the different choices possible at each sequential stage of the synthesis. For these techniques to be successful, it is necessary for the compounds to be amenable to methods by which one can determine the structure of the compounds so made. Examples of such techniques include, the technique of Brenner and Lerner (*PNAS USA* 81: 5381–83 (1992)) and WO 93/20242, according to which oligonucleotides are produced in parallel with oligopeptides; the oligonucleotides function as genetic tags and are chemically linked to the oligopeptides, which are the compounds of interest. WO 93/06121 teaches methods for particles-based synthesis of random oligomers wherein identification tags on the particles are used to facilitate identification of the oligomer sequence synthesized. Ohlmeyer et al., (*Proc. Natl. Acad. Sci. USA,* 90, 10922–10926, 1993) discloses a detachable tagging system.

SUMMARY OF THE INVENTION

The present invention relates to combinatorial libraries of compounds optionally encoded with tags, and to the use of these libraries in assays to discover biologically active compounds. The present invention also relates to seven libraries of compounds containing hydroxy amides amides and the use of the libraries to identify biologically active members by screening bioassays.

In one aspect, the invention relates to a combinatorial chemical library comprising a plurality of members of the Formula I:

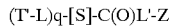

or

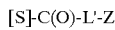

wherein:

[S] is a solid support;
T-L- is an identifier residue;
-L'-Z is a linker/compound residue;
q is zero (formula I') or 1–30;

Z is

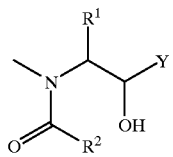

$R^1$ is $C_1$ to $C_{20}$ hydrocarbon, substituted aryl, substituted aralkyl or $(CH_2)_n NHC(O)R^3$;

$R^2$ is $C_1$ to $C_{20}$ hydrocarbon, substituted alkyl, substituted aryl, heteroaryl, aryloxyalkyl, alkoxyalkyl, or —CH($R^4$)OC(O)NHR$^3$;

$R^3$ is $C_1$ to $C_{20}$ hydrocarbon or substituted aryl;

$R^4$ and $R^5$ are independently lower alkyl or aryl;

n is 1–4;

Y is chosen from —P(O)(OR$^6$)(OR$^7$), —CH(OH)—COR$^8$, —CH$_2$CH=CH$_2$, —CH$_2$CH(OH)CH$_2$OH, —CH$_2$CHO, —CH$_2$CH$_2$OH, —CH$_2$CH$_2$OC(O)NHR$^{26}$, —CH$_2$CH$_2$NR$^{27}$R$^{28}$, and

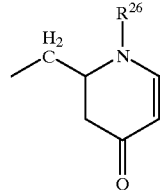

$R^6$ and $R^7$ are independently $C_1$ to $C_{20}$ hydrocarbon or —(CH$_2$)$_n$R$^9$, or, when $R^6$ and $R^7$ are methylene radicals, they may fuse to form a ring;

$R^8$ is chosen from —NHR$^{10}$, —N(lower alkyl)R$^{10}$ —NH(CH$_2$)$_n$R$^{11}$, —NHCH(R$^{12}$)C(OH)(R$^{13}$)(R$^{14}$), —NHCH(R$^{15}$)C(O)R$^{16}$,

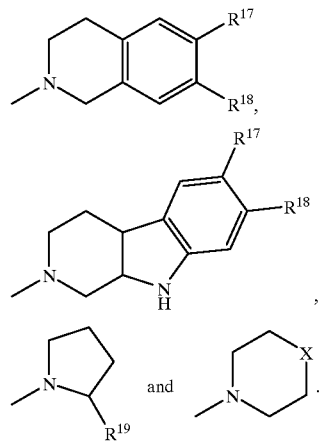

X is chosen from CH$_2$, O, S, NC(O)O-alkyl, NC(O)-aralkyl, NC(O)-aryl, NC(O)-heteroaryl,

[Structures: 2-quinolinyl; N(CH₂)ₙ-benzodioxole; 2-pyrimidinyl]

$R^9$ is chosen from halogen, perfluoroalkyl, and aryl;

$R^{10}$ is chosen from $C_1$ to $C_{20}$ hydrocarbon,

[Structure: indane with R²², R¹⁷, R¹⁸, R²⁰, R²¹]

[Structure: tetrahydronaphthalene with R¹⁷, R¹⁸, R²⁰, R²¹], and

[Structure: pyrrolidine with N—R²³]

$R^{11}$ is chosen from substituted alkyl, heteroaryl, heterocycloalkyl, —O(CH₂)ₙOH, —NR⁵alkyl, aryl-SO₂NH₂, —CH₂NHSO₂-aryl, and

[Structure: —(CH₂)ₙ—N-pyrrolidinone];

$R^{12}$ is chosen from hydrogen, $C_1$ to $C_{20}$ hydrocarbon, substituted alkyl, —C(O)NH₂, —C(O)NH-alkyl, —C(O)NH-aryl, and —C(O)NH-aralkyl;

$R^{13}$ and $R^{14}$ are independently H, alkyl, or aryl;

$R^{15}$ is chosen from hydrogen and $C_1$ to $C_{20}$ hydrocarbon;

$R^{16}$ is chosen from —NHalkyl and —NHCHR²⁴CONHR²⁵;

$R^{17}$, $R^{18}$, $R^{20}$, $R^{21}$ are independently H, alkyl, halo, or alkoxy;

$R^{19}$ is chosen from H, —(CH₂)ₙOH, —(CH₂)ₙOMe, and CONHR²³;

$R^{22}$ is chosen from H and OH;

$R^{23}$ is chosen from H, $C_1$ to $C_{20}$ hydrocarbon and substituted aryl;

$R^{24}$ and $R^{25}$ are H or $C_1$ to $C_{20}$ hydrocarbon;

$R^{26}$ is chosen from H, lower alkyl, aralkyl and aryl;

$R^{27}$ is chosen from H, alkyl, CH₂(CH₂)ₙ-alkoxy, arylalkyl, heteroarylalkyl

[Structures: indanyl; tetrahydrofurfuryl-CH₂; (CH₂)₃-N-pyrrolidinone; CH₂CH(aryl)OCH₃; CH₂CH(alkyl)OCH₃ and CH₂CH(Ph)₂]

$R^{28}$ is chosen from H, —C(O)R²⁹, —SO₂R³⁰, —C(O)NHR³⁰, alkyl, arylalkyl, and heteroarylalkyl;

or together —NR²⁷R²⁸ form a nitrogenous heterocycle chosen from: piperidine, 3-substituted-piperidine, 4-substituted-piperidine, 4-substituted-piperazine, morpholine, pyrrolidine, 2-substituted-pyrrolidine, tetrahydroisoquinoline and substituted tetrahydroisoquinoline;

$R^{29}$ is chosen from alkyl, arylalkyl, heteroarylalkyl, aryl, heteroaryl and —CH₂O-aryl; and $R^{30}$ is chosen from alkyl, arylalkyl and aryl.

Preferred libraries of Formula I are those wherein T'-L- is of the Formula II

[Structure II: acetylphenyl with OCH₃ and O—(CH₂)ₙ—Ar]    II wherein:

n=3–12;

Ar is halophenyl; and q=1–12.

More preferred libraries of Formula I are those wherein T'-L- is of the Formula II and n is 3–12 and Ar is a pentachlorophenyl.

Other preferred libraries of Formula I are those wherein -L'- is

[Structure: nitrophenyl-CH₂—]

such that the left-hand bond as shown is the point of attachment to —C(O)— the and the right hand bond is the point of attachment to -Z.

Depending on the choice of L' (see Table 1), the compounds or ligands -Z of Formula I may be detached by photolytic, oxidative, acidic, basic, or other cleavage techniques. For example, when -L'- is a residue of formula (a), photolytic cleavage may be represented by:

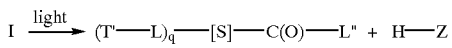 

wherein L" is the residue from L' and the genus H-Z may be represented by Formula III:

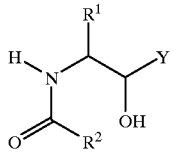

A preferred embodiment of the invention is a library comprising members of Formula I wherein $R^1$ is selected from the 15 residues of the amines of Table 2-1; $R^2$ is selected from the 31 residues of the acids of Table 2-2; and Y is $P(O)(OR^6)(OR^7)$, as selected from the 7 phosphinate residues of Table 2-3.

Another preferred embodiment of the invention is a library comprising members of Formula I wherein $R^1$ and $R^2$ are selected as above from Tables 2-1 and 2-2; Y is —CH(OH)—$COR^8$; and $R^8$ is selected from the residues of the amines in Table 2-4.

Other preferred embodiments of the invention are libraries comprising members of Formula I wherein $R^1$ and $R^2$ are selected as above from Tables 2-1 and 2-2 and Y is one of —CH—CH=$CH_2$, —$CH_2CH(OH)CH_2OH$, —$CH_2CHO$, and —$CH_2CH_2OH$.

Another preferred embodiment of the invention is a library comprising members of Formula I wherein $R^1$ and $R^2$ are selected as above from Tables 2-1 and 2-2, Y is —$CH_2CH_2OC(O)NHR^{27}$ and $R^{27}$ is lower alkyl or phenyl.

Another preferred embodiment of the invention is a library comprising members of Formula I wherein $R^1$ and $R^2$ are selected as above from Tables 2-1 and 2-2; Y is —$CH_2CH_2NR^{27}R^{28}$; $R^{27}$ is chosen from the residues of Table 2-7; an $R^{28}$ is chosen from the residues of Tables 2-9 to 2-11.

Another preferred embodiment of the invention is a library comprising members of Formula I wherein $R^1$ and $R^2$ are selected as above from Tables 2-1 and 2-2, Y is —$CH_2CH_2NR^{27}R^{28}$ and together —$NR^{27}R^{28}$ form a nitrogenous heterocycle chosen from the residues of Table 2-8.

Another aspect of the invention is the use of the combinatorial library described above in assays to discovery biologically active compounds or ligands of Formula III. Thus another aspect of the invention is a method of identifying a compound having a desired characteristic which comprises synthesizing a combinatorial library of Formula I and testing the library of Formula I, either attached to or detached from the solid supports, in an assay which identifies compounds of Formula III having the desired characteristic. A further aspect of the invention is determining the structure of any compound so identified.

It is within the scope of the present invention that chemical structures of compounds identified as having a desired characteristic can be determined by either decoding the tags (T, T'-L- of Formula I) or by deconvolution of the library (Smith et al., *BioMed. Chem. Lett.*, 4, 2821 (1994); Kurth et al., *J Org. Chem.*, 59, 5862 (1994); Murphy et al., *J. Am. Chem. Soc.*, 117, 7029 (1995); Campell et al., *J. Am. Chem. Soc.*, 118, 5381 (1995); and Erb et al., *Proc. Natl. Acad. Sci. USA*, 91, 11422 (1994)).

When q is zero, the resultant untagged libraries comprise members of Formula I':

[S]-C(O)-L'-Z    I' wherein the symbols are as defined for Formula I.

Another embodiment of the invention is a method of synthesizing a library comprising members of Formula VI

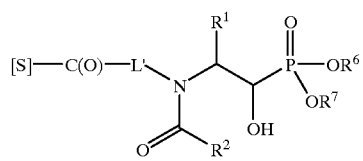

which comprises reacting a compound of Formula IV

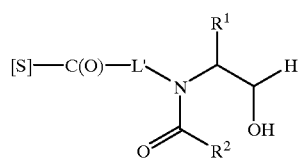

with iodoxybenzoic acid in a suitable solvent such as DMSO to give a compound of Formula V

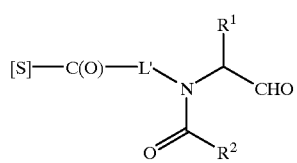

which in turn is reacted with a phosphinic acid dissolved in a suitable solvent such as DCM at 25° C. to produce a library of Formula VI.

Another embodiment of the invention is a method of synthesizing a library comprising members of Formula VII which comprises reacting a compound of Formula V

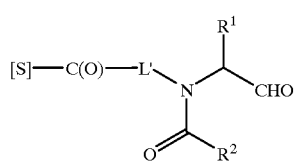

with a allyl bromide in the presence of indium metal in a suitable solvent such as THF, MeOH or water at 25° C. with sonication to produce a library of Formula VII

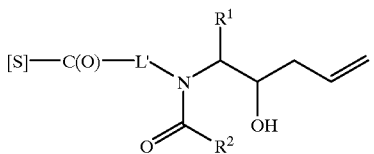

Another embodiment of the invention is a combinatorial library of chemical intermediates comprising members of the Formulae VIIIa through VIIId

[S]—C(O)—L'—N(COR²)C(O)CH(R¹)CH=CHCOOtB  VIIIa

C(O)—L'—N(COR²)C(O)CH(R¹)CH(OH)CH(OH)COOtBu  VIIIb

[S]—C(O)—L'—N(COR²)C(O)CH(R¹)CH(OAc)CH(OAc)COOH  VIIIc

[S]—L'N(COR²)C(O)CH(R¹)CH(OAc)CH(OAc)COR⁸  VIIId

Another embodiment of the invention is a method of synthesizing a library comprising members of Formula IX

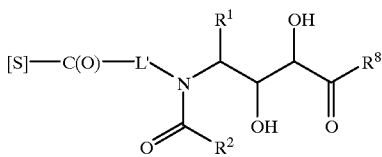

which comprises condensing a compound of Formula VIIIc

[S]-C(O)-L'-N(COR²)C(O)CH(R¹)CH(OAc)CH(OAc)COOH  VIIIc with a primary or secondary amine in the presence of a carboxylic acid activated by a reagent such as pentafluorophenyl trifluoroacetate in a suitable solvent such as pyridine to give intermediates of the formula VIIId.

[S]-L'N(COR²)C(O)CH(R¹)CH(OAc)CH(OAc)COR⁸  VIIId

Diacetate intermediate VIIId is in turn treated with hydrazine in a suitable solvent such as methanol.

DETAILED DESCRIPTION OF THE INVENTION

Abbreviations and Definitions

The following abbreviations and terms have the indicated meanings throughout:
Ac=Acetyl
BNB=4-bromomethyl-3-nitrobenzoic acid
BOC=t-butyloxy carbonyl
Bu=butyl
c-=cyclo
DBU=Diazabicyclo[5.4.0]undec-7-ene
DCM=Dichloromethane=methylene chloride=$CH_2Cl_2$
DIC=diisopropylcarbodiimide
DIEA=diisopropylethyl amine
DMAP=4-N,N-dimethylaminopyridine
DMF=N,N-dimethylformamide
DMSO=Dimethyl sulfoxide
DVB=1,4-divinylbenzene
FACS=fluorescence activated cell sorting
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
IBX=iodoxybenzoic acid
m-=meta
Me=methyl
NMO=N-methylmorpholine oxide
PEG=polyethylene glycol
Ph=phenyl
PhOH=phenol
Pfp=pentafluorophenol
r.t.=room temperature
sat'd=saturated
s-=secondary
t-=tertiary
TBS=tert-butyldimethylsilyl
TFA=trifluoroacetic acid
THF=tetrahydrofuran
TMOF=trimethyl orthoformate
TMS=trimethylsilyl "Alkyl" or "lower alkyl" is intended to include linear, or branched hydrocarbon structures and combinations thereof. "Alkyl means alkyl groups of from 1 to 20 carbon atoms. Examples of alkyl groups include methyl, ethyl, propyl, isopropyl, butyl, s-and t-butyl, pentyl, hexyl, octyl, and the like. Lower alkyl comprises alkyl of one to six carbons.

"Cycloalkyl" or "lower cycloalkyl" includes cycloalkyl groups of from 3 to 12 carbon atoms. Examples of "cycloalkyl" or "lower cycloalkyl" groups include c-propyl, c-butyl, c-pentyl, c-hexyl, 2-methylcyclopropyl, cyclopropylmethyl, cyclopentylmethyl, norbornyl, adamantyl, and the like.

"Alkenyl" is $C_2$–$C_8$ alkenyl of a linear, branched, or cyclic ($C_5$–$C_6$) configuration and combinations thereof. Examples of alkenyl groups include vinyl, allyl, isopropenyl, pentenyl, hexenyl, c-hexenyl, 1-propenyl, 2-butenyl, 2-methyl-2-butenyl, and the like.

"Alkynyl" is $C_2$–$C_8$ alkynyl of a linear or branched configuration and combinations thereof. Examples of alkynyl groups include ethyne, propyne, butyne, pentyne, 3-methyl-1-butyne, 3,3-dimethyl-1-butyne, and the like.

Hydrocarbon includes alkyl, cycloalkyl, alkenyl, alkynyl, aryl and combinations thereof. Examples include phenethyl, cyclohexylmethyl and naphthylethyl.

"Alkoxy" means alkoxy groups of from 1 to 8 carbon atoms of a straight, branched, cyclic configuration and combinations thereof. Examples of alkoxy groups include methoxy, ethoxy, propoxy, isopropoxy, cyclopropyloxy, cyclohexyloxy, and the like.

"Acylamino" means acylamino groups of from 1 to 8 carbon atoms of a straight, branched or cyclic configuration and combinations thereof. Examples of acylamino groups are acetylamino, butyrylarnino, cyclohexylcarbonylamino, and the like.

Halogen includes F, Cl, Br, and I, with F and Cl as the preferred groups.

"Halophenyl" means phenyl substituted by 1–5 halogen atoms. Halophenyl includes pentachlorophenyl, pentafluorophenyl, and 2,4,6-trichlorophenyl.

"Fluoroalkyl" refers to an alkyl residue in which one or more hydrogen atoms are replaced with F, for example: trifluoromethyl, difluoromethyl, and pentafluoroethyl.

"Aryl" and "heteroaryl" mean a 5- or 6-membered aromatic or heteroaromatic ring containing 0–3 heteroatoms selected form O, N, and S; a bicyclic 9- or 10-membered aromatic or heteroaromatic ring system containing 0–3 heteroatoms selected from O, N, and S; or tricyclic 13- or 14-membered aromatic or heteroaromatic ring system containing 0–3 heteroatoms selected from O, N, and S; each of which rings is optionally substituted with one or more of lower alkyl, substituted alkyl, alkenyl, alkynyl, =O, $NO_2$, halogen, hydroxy, alkoxy, alkoxyethoxy, cyano, $NR^{31}R^{31}$, acylamino, perfluoroalkyl, phenyl, benzyl, phenoxy, naphthyloxy, aryloxy, benzyloxy, heteroaryl, and heteroaryl, and heteroaryloxy. Each of the foregoing phenyl, benzyl, phenoxy, benzyloxy, heteroaryl, and heteroaryloxy substituents is optionally substituted with 1–3 substituents selected from lower alkyl, alkenyl, alkynyl, halogen, hydroxy, alkoxy, cyano, phenyl, benzyl, benzyloxy, caboxamido, heteroaryl, heteroaryloxy, $NO_2$, and $NR^{31}R^{31}$, in which $R^{31}$ is independently H, alkyl, cycloalkyl, aryl, aralkyl, or in which $R^{31}R^{31}$ are fused to form a cyclic ring with nitrogen.

The aromatic 6- to 14-membered carbocyclic rings include benzene, naphthalene, indane, tetralin, and fluorene and the 5- to 10-membered aromatic heterocyclic rings include imidazole, pyridine, indole, thiophene, benzopyranone, thiazole, furan, benzimidazole, quinoline, isoquinoline, quinoxaline, pyrimidine, pryrazine, tetrazole, and pyrazole.

"Arylalkyl" denotes a residue comprising an alkyl attached to an aryl ring. Examples include benzyl, phenethyl, 4-chlorobenzyl, and the like.

"Heteroarylalkyl" denotes a residue comprising an alkyl attached to a heteroaryl ring. Pyridinylmethyl and pyrimidinylethyl, are examples of heteroarylalkyl residues.

"Heterocycloalkyl" means a cycloalkyl where one to two of the methylene ($CH_2$) groups is replaced with a heteroatom such as O, NR(R=H, alkyl), S and the like. When two heteroatoms are separated by a single carbon, the resulting heterocycloalkyls tend to be unstable in aqueous solutions and are therefore not preferred. Examples of heterocycloalkyls include: tetrahydrofuranyl, piperidine, dioxanyl, and the like.

"Carboxyalkyl" means —C(O)R where R is alkyl.

"Substituted" when modifying residues such as alkyl, alkenyl, alkynyl, cycloalkyl, or heterocycloalkyl means those residues wherein hydrogen atoms are replaced by halogen, hydroxy, lower alkoxy, carboxy, carboalkoxy, carboxamido, cyano, carbonyl, $NO_2$, $NR^{31}R^{31}$; $—SR^{31}$, $—SO_2R^{31}$, $—SO_2R^{31}$, acylamino, amidino, guanidino, ureido, aryl, heteroaryl, phenyl, aralkyl, phenoxy, benzyloxy, naphthyloxy, aryloxy, heteroaryloxy.

The linkers may be any component capable of being selectively cleaved to release both T and Z from the solid support. See, e.g., Greene and Wuts, "Protective Groups in Organic Synthesis," 2nd ed., Wiley, 1991. Specific linkers L' are depicted in Table 1 (note that -L-=—C(O)L'- or —$CH_2$—C(O)L'-), which also shows cleavage reagents. In designing a synthetic scheme, L and L' are chosen such that they are orthogonally reactive, i.e., they allow for removal of either T or Z (where T=TOH) without removal of the other, since simultaneous cleavage of both T and Z from the solid support is disadvantageous. In the structures as shown, the left-hand bond is the point of attachment to the solid support (via —C(O)— for L' and —C(O)— or —$CH_2$C(O)— for L) and the right-hand bond is the point of attachment to either T or Z.

The tags of this invention, T, are chemical entities which possess several properties: they are detachable from the solid supports, preferably by photolysis or oxidation; they are individually differentiable, and preferably separable; they are stable under the synthetic conditions; they are capable of being detected at very low concentrations, e.g., $10^{-18}$ to $10^{-9}$ mole. Preferred tags are identifiable with readily available equipment which does not require sophisticated technical capabilities to operate, and they are relatively economical. The tags may be structurally related or unrelated, e.g., a homologous series, repetitive functional groups, related members of the Periodic Chart, different isotopes, combinations thereof, and the like. At the end of the combinatorial synthesis, to each solid support, there will usually be attached at least 0.01 femtomol, usually 0.001–50 pmol, of each tag. The tags may be aliphatic, alicyclic, aromatic, heterocyclic, or combinations thereof. Distinguishing features may be the number of repetitive units, such as methylene groups in an alkyl moiety; alkyleneoxy groups in a polyalkyleneoxy moiety; halo groups in a polyhalo compound; α- and/or β-substituted ethylene groups where the substituents may be alkyl groups, alkoxy, carboxy, amino, halo, or the like; isotopes; etc. Suitable tags and methods for their employment are described in U.S. Pat. No. 5,565,324, the entire disclosure of which is incorporated herein by reference.

The materials upon which the combinatorial syntheses of the invention are performed are referred to as solid supports, beads, and resins. These terms are intended to include:

(a). beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and (b). soluble supports such as polyethylene glycol or low molecular weight non-cross-linked polystyrene.

Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R) or (S), or as (D) or (L) for amino acids. The present invention is meant to include all such possible diastereomers as well as their racemic and optically pure forms. Optically active (R) and (S), or (D and L), isomers may be prepared using chiral synthons or chiral reagents, or resolved using conventional techniques. When the compounds described herein contain olefinic double bonds or other centers of geometric asymmetry, unless specified otherwise, it is intended to include both E and Z geometric isomers. Likewise, all tautomeric forms are intended to be included.

Utility

The library of the present invention is useful as a screening tool for discovering new lead structures by evaluation across an array of biological assays, including the discovery of selective inhibition patterns across isozymes. The library is thus a tool for drug discovery; i.e., as a means to discover novel lead compounds by screening the library against a variety of biological targets and to develop structure-activity relationships (SAR) in large families of related compounds. The library may be tested with the ligands attached to the solid supports as depicted in Formula I or I', or the compounds Z may be detached prior to evaluation. With the compounds of Formula I or I', screening assays such as FACS sorting and cell lawn assays may be used. A particularly useful lawn assay is described in U.S. patent application Ser. No. 08/553,056 (filed Nov. 3, 1995), the disclosure of which is incorporated herein by reference. When a compound is detached prior to evaluation, its relationship to its solid support is maintained, for example, by location within the grid of a standard 96-well plate or by location of activity on a lawn of cells. Whether the compounds are tested attached or detached from the solid supports, the tags attached to solid support associated with bioactivity may then be decoded to reveal the structural or synthetic history of the active compound (Ohlmeyer et al., *Proc. Natl. Acad. Sci., USA*, 90 10922–10926, December 1993 and Still et al., Complex Combinatorial Chemical Libraries Encoded with Tags, WO 94/08051) or, alternatively, the structures may be determined by deconvolution. The usefulness of such a library as a screening tool is demonstrated by Burbaum et al., *Proc. Natl. Acad. Sci., USA*, 92 6027–6031, June 1995, who describe the assaying of encoded combinatorial libraries for, e.g., carbonic anhydrase inhibition. Even if no compounds are found to be active in a given screen, such lack of activity often provides useful SAR information.

Assays for Determining Biological Activity

Assays for evaluating the compounds of the present invention are well known in the art. Although one usually does not know a priori in which specific assays a particular library compound or group of library compounds will have activity, useful screening systems for use in assaying libraries of the format described herein, in order to identify activity with respect to a wide variety of enzymes and molecule targets have been developed and are illustrated by the following example.

1. Xanthine Oxidase Inhibition

The following materials are used:

3.9 $\mu$M hypoxanthine 0.3 mM 4-aminoantipyrene 2 mM 3,5-dichloro-2-hydroxybenzenesulfonate 50 mM sodium phosphate buffer, pH 7.5

5 U/mL horseradish peroxidase (Sigma P-6782, 5500 U/5 mg)

3 nM xanthine oxidase (buttermilk, Sigma X-4500, 16 U/mL)

Reactions are carried out in 24 $\mu$L total volume in 96-well U-bottom polypropylene microtiter dishes (Costar) containing the test compounds 8 $\mu$L of sodium phosphate buffer, pH 7.5, is added to each well. A substrate mixture is prepared on ice by mixing 0.53 mL sodium phosphate buffer, 0.4 mL 4-aminoantipyrene (0.61 mg/mL), 0.4 mL 3,5-dichloro-2-hydroxybenzenesulfonate (5.3 mg/mL), 4 $\mu$L horseradish peroxidase (Sigma P-6782, 5500 U/5 mg), and 128 $\mu$L hypoxanthine 920 $\mu$g/mL. 8 $\mu$L of the substrate mixture is then pipetted into each well. 8 $\mu$L xanthine oxidase (buttermilk, 9.0 nM, Sigma X-4500, 16 U/mL) in sodium phosphate buffer, pH 7.5 (or buffer alone as a control) is added last, directly into the reaction mixture. The plates are pulse-spun briefly in a tabletop centrifuge before reading absorbance. Absorbance is read using a dual kinetics program (490 minus 650 nm) for 15 min. at r.t. without automix, in a microplate reader (Molecular Devices Thermomax). Initial rates are calculated (Vmax program) and compared to those of reactions without inhibitor.

2. Plasmepsin II Inhibition

The assay mix contained 50 mM sodium acetate (pH 5.0), 1 mg/mL BSA, 0.01% Tween 20, 12.5% glycerol, 18% DMSO and 12 $\mu$M plasmepsin substrate. Twenty five $\mu$L of the assay mix was added to each well of a 96-well microtiter plate containing dried down bead eluate or empty control wells. The plates were then sonicated and mixed. 25 $\mu$L of 8 nM plasmepsin II, in 50 mM sodium acetate (pH 5.0), 1 mg/mL BSA, 0.01% Tween 20, and 12.5% glycerol, was added to the assay mix. The final concentrations were 4 nM plasmepsin II, 6 $\mu$M plasmepsin substrate, 9% DMSO, 50 mM sodium acetate (pH 5.0), 1 mg/mL BSA, 0.01% Tween 20, and 12.5% glycerol. The reaction was incubated for 10 minutes at 25° C. and then quenched by the addition of 25 $\mu$L of 1 M Tris (pH 8.5) and 50% DMSO to achieve a final concentration of 0.33 M Tris and 23% DMSO. The EDANS fluorescence was measured using a Tecan, SLT FluoStar fluorescence plate reader with an excitation filter of 350 nm and an emission filter 510 nm. The background was determined by 25 $\mu$L of 50 mM sodium acetate (pH 5.0), 1 mg/mL BSA, 0.01% Tween 20, and 12.5% glycerol without enzyme.

Other examples of assay methods for evaluating the compounds of the present invention are disclosed in the following references which are incorporated herein by reference:

ACE Inhibition—Holmquist et al., "A Continuous Spectrophotometric Assay for Angiotensin Converting Enzyme", *Anal. Biochem.*, 95, 540–548 (1979).

Thrombin Inhibition—Lottenberg et al., "Assay of Coagulation Proteases Using Peptide Chromogenic and Fluorogenic Substrates", *Meth. in Enzymol.*, 80, 341–361, (1981).

Carbonic Anhydrase Inhibition—Maren and Couto, "The Nature of Anion Inhibition of Human Red Cell Carbonic Anhydrases", *Archiv. of Biochem. and Biophy.*, 196, No. 2, September, 501–510 (1979).

Carbonic Anhydrase Inhibition—Ponticelo et al., "Thienothiopyran-2-sulfonamides: A Novel Class of Water-Soluble Carbonic Anhydrase Inhibitors", *J. Med. Chem.*, 30, 591–597 (1987).

Methods of Synthesis

The compounds of the present invention can be prepared according to the following methods. During each step in the syntheses that follow, each solid support upon which a compound is being synthesized, is uniquely tagged to define the particular chemical event(s) occurring during that step. The tagging is accomplished using identifiers such as those of Formula II, which record the sequential events to which the support is exposed during the synthesis. Tagging thus provides a reaction history for the compound produced on each support. The identifiers are used in combination with one another to form a binary or higher order encoding scheme permitting a relatively small number of identifiers to encode a relatively large number of reaction products. For example, when used in a binary code, N identifiers can encode up to $2^N$ different compounds and/or conditions. By associating each variable or combination of variables at each step of the synthesis a combination of identifiers which uniquely define the chosen variables such as reactant, reagent, reaction conditions, or combinations of these, one can use identifiers to define the reaction history of each solid support.

In carrying out the syntheses, one begins with at least $10^4$, desirably at least $10^7$, and generally not exceeding $10^{15}$ solid supports. Depending on the predetermined number of $R^1$ choices for the first step, one divides the supports accordingly into as many containers. The appropriate reagents and reaction conditions are applied to each container and the combination of identifiers which encode for each $R^1$ choice is added and attached. The reagents are commercially available or are prepared by means well known in the art. Depending on the chemistries involved, the tagging may be done prior to, concomitantly with, or after the reactions which comprise each choice. As a control, sample supports may be picked at any stage and a portion of their tags cleaved from the sample supports. As needed, one may wash the beads free of any excess reagents or byproducts before proceeding. At the end of each step, the supports are combined, mixed, and again divided, this time into as many containers as pre-determined for the number of $R^2$ choices for the second step in the synthesis. This procedure of dividing, reacting, tagging, and remixing is repeated until the combinatorial synthesis is completed.

A. Scheme 1: Derivatizing Resin with Bis-Fmoc Lysine

A batch of amino-functionalized PEG-grafted polystyrene beads such as TentaGel™ 1 amine may be modified with bis-Fmoc lysine 2 to increase the available reaction sites for ligand attachment. Bis-Fmoc lysine 2 is coupled to amino-functionalized TentaGel 1 by amide bond formation. Coupling is achieved by reacting a suspension of 1 in DMF with 2, HOBt and DIC. The suspension is shaken overnight, then drained or filtered and washed in succession with DMF, methanol and DCM. The derivatized resin 3 so obtained is dried overnight under vacuum.

The lysine loaded resin 3 is divided into a pre-determined number of reaction vessels for identification through tagging. In this instance, since fifteen amino-alcohols are used in the first combinatorial step, in fifteen reaction vessels are placed equal portions of resin. Identifiers are added prior to addition of the photo-labile linker and residues $R^1$.

Unique tagging of the supports in each reaction vessel is achieved with combinations of additional identifiers encoded in a binary scheme, e.g., as depicted in Table 2-1, for the subsequent fifteen choices of $R^1$. The identifiers are attached by adding a solution of up to two identifiers in DCM (in a 7.5–15% wt./wt. identifier: solid support ratio, depending on the signal strength of the identifier) to a batch of supports suspended in ethyl acetate or DCM and shaking the mixture for 0.5–1 hour. A dilute solution of rhodium trifluoroacetate dimer is added and the mixture is immediately shaken overnight, then washed in DCM, methanol and DCM. The procedure is repeated as necessary to add additional identifiers. For the purposes of simplicity, the identifiers are not shown in the schematics.

B. Scheme 2

The Fmoc-protecting group on resin 3 is removed and 4-bromomethyl-3-nitrobenzoic acid (BNB) is attached. This is accomplished by the following method. A suspension of tagged resin 3 in 1:1 piperidine:DMF is shaken about 1.5 hr, then washed with DMF, methanol, DCM. This bis-amine resin 4 is suspended in DMF, and treated with a solution of BNB, HOBt, DIC in DMF. The suspension is shaken overnight, then drained and the resin is washed with DCM. The tagged BNB resin 6 is dried overnight in vacuum. This is repeated for each of the fifteen reaction vessels.

C. Scheme 3

The fifteen batches of tagged BNB resin 6 are reacted with a unique, protected amino-alcohol (e.g., see Table 2-1) to generate compound 7. The coupling of each amine occurs through displacement of the linker bromide and formation of a new carbon-nitrogen bond. Two cycles of reactions are performed to ensure complete conversion. In the first cycle, the amine is added to a suspension of resin 6 in THF and the mixture is shaken overnight. The mixture is drained and the resin is washed with THF. The THF solution containing the excess amine is then concentrated, taken up in DCM, washed with aqueous sodium bicarbonate, dried over sodium sulfate and concentrated. The residue is taken up in DMF and reacted with the same resin for the second reaction cycle. Lithium iodide is added to the suspension and the mixture is shaken overnight. The suspension is drained and the resin is washed with DMF, methanol, DCM and dried overnight in vacuum. This is repeated for each of the fifteen reaction vessels. After coupling, a small portion of each batch of resin may be removed and titrated with picric acid to determine the extent of amine loading as a quality control for the reaction in this combinatorial step.

The protected amino alcohols are obtained by reduction of amino acids by borane in THF, followed by silylation using tert-butyldimethylsilyl chloride and imidazole in DMF according to the procedure of Brown [*J. Am. Chem. Soc.* 82, 3866 (1960)]. The amino acids are commercially available.

D. Scheme 4

The amines 7 are pooled, mixed, and divided into a pre-determined number of reaction vessels. In this instance, since thirty-one acylating agents are used in the second combinatorial step, in thirty-one reaction vessels are placed equal portions of resin.

The mixtures of amines 7 are coupled with an acid corresponding to one of the thirty one $R^2$ choices in Table 2-2, by amide bond formation. This is accomplished by one of two procedures. Procedure A: Each acid depicted in entries 1–27 is first converted to its acid chloride by standard conditions (oxalyl chloride in DCM with catalytic DMF, 40° C.). Each acid chloride is added to a suspension of amine resin 7 in pyridine. The mixture is shaken overnight, drained and the resin is washed with DMF, methanol and DCM. This is repeated for the first twenty seven reaction vessels.

In procedure B, the remaining four reaction vessels containing the pooled amine 7 are all coupled with the same acid chloride 9, but after removal of the chloroacetyl protecting group, the resulting four mixtures of alcohols are each condensed with one of the four isocyanates in Table 2-3 to form carbamates. This is accomplished by the following method. The amines 7 are treated with acid chloride 9 in pyridine for 1.5 hr. The resin is washed with DMF, methanol and DCM, and the chloroacetyl protecting group on 10 is cleaved by treatment with a solution of hydrazine in methanol for 1 hr. After washing of the resin with DMF, methanol and DCM, each mixture of alcohols 11 is reacted with one of the $R^{2'}$ isocyanate in Table 2-3. The isocyanate is added to a suspension of the resin 11 in acetonitrile along with a catalytic amount of DBU. The mixture is shaken overnight, then drained and the resin is washed with DMF, methanol, DCM. The procedure is repeated for the four isocyanates and in this fashion the acids of entries 28–21 (Table 2-2) are coupled to the amine resin.

Unique tagging of the supports in each reaction vessel is achieved with combinations of additional identifiers encoded in a binary scheme, e.g., as depicted in Tables 2-2 for the 31 choices of $R^2$. The identifiers are attached by adding a solution of up to two identifiers in DCM (in a 7.5–15% wt./wt. identifier: solid support ratio, depending on the signal strength of the identifier) to a batch of supports suspended in ethyl acetate or DCM and shaking the mixture for 0.5–1 hr. A dilute solution of rhodium trifluoroacetate dimer is added and the mixture is immediately shaken overnight, then washed in DCM, methanol, DCM. The procedure is repeated as necessary to add additional identifiers.

E. Scheme 5

The resin is mixed and the conversion of the silyl ether 8 to the corresponding aldehyde by deprotection and oxidation is accomplished on all the resin. The protected alcohols 8 are treated with dilute hydrochloric acid in methanol for 5–8 hr to remove the t-butyldimethylsilyl protecting group. The resin is then washed with DMF, methanol and DCM. The resulting alcohols 12 are oxidized to the corresponding aldehydes by the following method. To a suspension of the resin 12 in DMSO is added a solution of IBX (13) in DMSO and the mixture is shaken overnight. The suspension is drained, the resin is washed with DMSO and treated with another solution of IBX in DMSO for 4 hr. The mixture is then drained and the resin is washed with DMSO, methanol, DCM and dried overnight in vacuo.

The mixed aldehydes 14 are then divided into three portions. One portion is taken through the chemistry described in Scheme 6 producing a library as given in Example 1. Another portion is taken through the chemistry described in Schemes 7 and 8, producing a library as given in Example 3. Finally another portion is taken through the chemistry described in Schemes 9–13, producing five libraries as given in Examples 5, 7, 9, 11 and 13. Thus three libraries are produced which share synthons $R^1$ and $R^2$ in common with one another.

F. Scheme 6

In this chemistry, the mixed and pooled resin bound aldehydes 14 are split into a pre-determined number of reaction vessels. In this instance, since seven phosphites are used in the third combinatorial step, in seven reaction vessels are placed equal portions of resin. In each vessel the resin is reacted with one of the seven dialkyl phosphites in Table 2-4 in the following manner. To a suspension of the resin in DCM is added the phosphite followed by triethylamine and the mixture is shaken overnight. The suspension is drained and the resin is washed with DMF, methanol, DCM. This procedure is repeated for each of the seven phosphites to complete the synthesis of the library resin compound 15 (illustrated hereinafter by Example 1). The resultant resin batches may then be tagged as described above or retained separately as sub-libraries. Amides of Formula III may be cleaved from resin compounds 15 by exposing them to UV light (ca. 360 nm) for 15–180 minutes at 25–50° C. in a suitable solvent such as methanol.

G. Scheme 7

With Scheme 8, Yields a Library of Compounds as in Example 3

In this chemistry, the mixed and pooled resin bound aldehydes 14 (from Scheme 5) are converted to diacetate esters 19 by a Wittig reaction, followed by catalytic dihydroxylation of the alkenes and protection of the diols as a diacetates. The resin bound aldehydes 14 in suspension in THF are reacted with (t-butoxycarbonylmethylene)-triphenylphosphorane (16) overnight. After washing with THF, methanol and DCM, the α,β-unsaturated esters 17 are suspended in acetone-water (1:1 mixture) and NMO is added along with a solution of osmium tetroxide in water. The mixture is shaken overnight, drained and the resin is washed with water, pyridine, DMF, methanol and DCM. Protection of the diol 18 is accomplished by treatment of the resin with a solution of acetic anhydride in pyridine containing a catalytic amount of DMAP for 18 hr. The resin is subsequently washed with DMF, methanol and DCM and dried overnight in vacuum.

H. Scheme 8

The mixture of resin 19 is split into a pre-determined number of reaction vessels. In this instance, since fifty amines are used in the third combinatorial step, in fifty reaction vessels are placed equal portions of resin. In each flask, the ester-diacetate 19 is converted to the corresponding acid, which is then coupled with one of the amines in table 2-5. Deprotection of the diol 23 then leads to the library resin 24. Hydrolysis of ester 19 is accomplished by treatment with neat TFA for 2 hr. The resin is then washed with DMF, methanol and DCM, and suspended in a small amount of a 1:1 mixture of DMF:pyridine. Pentafluorophenyl trifluoroacetate is added along with pentafluorophenol, the mixture is shaken 1 hr at room temperature and drained. The resin bound activated ester 22 is washed briefly with DMF and treated overnight with a DMF solution of one of the amine $R^8$ in table 2-5. After washing with DMF, methanol and DCM, the amide-diacetate 23 is shaken 2 hr in a solution of hydrazine in methanol, to afford resin bound diol 24 which is washed with DMF, methanol and DCM and dried overnight in vacuum. This procedure is repeated for each of the fifty amines to complete the synthesis of the library resin compound 24 (illustrated hereinafter by Example 3). The resultant resin batches may then be tagged as described above or retained separately as sub-libraries. Amides of Formula III may be cleaved from resin compounds 24 by exposing them to UV light (ca. 360 nm) for 15–180 minutes at 25–50° C. in a suitable solvent such as methanol.

I. Scheme 9

In this chemistry, the mixed and pooled resin bound aldehydes 14 are placed into a reaction vessel. The resin is reacted with allyl bromide and indium metal in the following manner. To a suspension of the resin and powdered indium metal in THF and water is added allyl bromide. The heterogenous mixture is sonicated for approximately 6 h after which time a milky white precipitate forms and the pH drops to pH3 and sonication is continued for another 1.5 hr. The resin is drained and the resin is washed with water, THF and DCM. Amides of Formula III may be cleaved from resin compounds 25 by exposing them to UV light (ca. 360 nm) for 15–180 minutes at 25–50° C. in a suitable solvent such as methanol.

J. Scheme 10

In this chemistry, the mixed pooled resin bound allyl alcohols 25 are placed into a reaction vessel. The resin is suspended in acetone and water to which osmium tetroxide and methylmorpholine-N-oxide (NMO) is added. The mixture is shaken for 12 h at room temperature. The resin is drained and washed with water, DMF, MeOH, and DCM. Amides of Formula III may be cleaved from resin compounds 26 by exposing them to UV light (ca. 360 nm) for 15–180 minutes at 25–50° C, in a suitable solvent such as methanol.

K. Scheme 11

In this chemistry, the mixed pooled resin bound triols 26 are placed into a reaction vessel. The resin is suspended in water to which an aqueous solution of sodium periodate is added. The mixture is shaken for 5 min at room temperature. The resin is drained and treated with aqueous periodate thrice more. The resin is finally washed with water, MeOH, and DCM and dried in vacuo. The resin is suspended THF to which a THF solution of lithium borohydride is added.

After 20 min the resin is drained and washed with THF, MeOH, and DCM. Amides of Formula III may be cleaved from resin compounds 27 by exposing them to UV light (ca. 360 nm) for 15–180 minutes at 25–50° C. in a suitable solvent such as methanol.

L. Scheme 12

In this chemistry, the mixed pooled resin bound allylic alcohols 25 are placed into a reaction vessel. The resin is suspended in DCM and cooled in an ice bath. 2,6-Lutidine is then added followed by the silylating reagent, tert-butyldimethylsilyl trifluoromethanesulfonate. After 5 min the ice bath is removed and the reaction mixture warmed to room temperature and shaken for approximately 2 hours. The resin is drained and washed with DCM and MeOH and then dried to give the silyl ether intermediate 28.

This intermediate 28 in turn is dihydroxylated using osmium tetroxide as described above in J. Scheme 10 to give the diol intermediate 29. The diol is cleaved using sodium periodate as in K. Scheme 11 to give the aldehyde intermediate 30. This intermediate 30 is a key intermediate for the synthesis of library compounds 32–37.

The resin bound aldehydes 30 are reduced to the corresponding alcohol with lithium borohydride in similar fashion as described in K. Scheme 11 to give intermediate alcohols 31 which in turn are reacted with one of two isocyanates (Table 2-6). The reaction with the isocyanate is carried out by shaking a suspension of 30 in acetonitrile and adding the isocyanate then shaking for 12 h. After draining the solvent, a solution of 1% HCl in MeOH is added and the suspension is shaken for 4.5 h to remove the silyl protecting group. This affords the carbamates 32.

The resin bound aldehydes 30 are reductively aminated by shaking a suspension of resin in neat trimethyl orthoformate in the presence of a primary amine (Table 2-7) or a secondary amine (Table 2-8) for some 15 min and then draining the reaction mixture and adding 5% acetic acid in MeOH and more of the amine along with sodium cyanoborohydride. After shaking for 12 h, the resin is drained and washed with MeOH and water. In the case where secondary amines are used (Table 2-8), the resin is treated with 1% HCl in MeOH as above to remove the silyl protecting group to give amines 33. Amides of Formula III may be cleaved from resin compounds 33 by exposing them to UV light (ca. 360 nm) for 15–180 minutes at 25–50° C. in a suitable solvent such as methanol.

In the case where primary amines are used (Table 2-7) and the resin bound amines 34 are produced, the resin is subsequently treated with one of several derivatizing reagents. For example, in those cases where the reductive amination of 30 is carried out using amines 5–13 (see Table 2-7, amines 5–13), then the resin is further reacted with either methyl sulfonyl chloride or acetic anhydride (Table 2-11). This is done by shaking the resin in DIEA-DCM and DMAP with one of the amine derivatizing reagents for 12 h. After the reaction mixture is drained and washed with MeOH, DCM, and 1% HCl in MeOH, it is suspended in 1% HCl in MeOH as above to remove the silyl protecting group to give amines 35. Amides of Formula III may be cleaved from resin compounds 35 by exposing them to UV light (ca. 360 nm) for 15–180 minutes at 25–50° C. in a suitable solvent such as methanol.

Alternatively, in those cases where the reductive amination of 30 is carried out using amines 2–4 (see Table 2-7, amines 2–4), then the resin is further reacted with either methyl sulfonyl chloride, phenyl sulfonyl chloride, acetic anhydride or benzoyl chloride (Table 2-10). This is done by shaking the resin in DIEA-DCM and DMAP with one of the amine derivatizing reagents for 12 h. After the reaction mixture is drained and washed with MeOH, DCM, and 1% HCl in MeOH, it is suspended in 1% HCl in MeOH as above to remove the silyl protecting group to give amines of formula 35, which may be cleaved from the resin by exposing them to UV light (ca. 360 nm) for 15–180 minutes at 25–50° C. in a suitable solvent such as methanol.

As a final alternative, in those cases where the reductive amination of 30 is carried out using methylamine (see Table 2-7, amines 1), then the resin is further reacted with either one of several derivatizing reagents as presented in Table 2-9. This is accomplished using the acylation, urea formation, reductive amination conditions as described above. After the reaction mixture derivatized, it is drained and washed with MeOH, DCM, and 1% HCl in MeOH. The resin is suspended in 1% HCl in MeOH as above to remove the silyl protecting group to give the corresponding amides, which may be cleaved from the resin by exposing them to UV light (ca. 360 nm) for 15–180 minutes at 25–50° C. in a suitable solvent such as methanol.

M. Scheme 13

In this chemistry, the mixed pooled resin bound aldehydes 30 are placed into a reaction vessel. The resin is suspended with neat trimethyl orthoformate and a primary amine. In this case benzyl amine is used. After shaking for 15 min, the resin is drained, washed with DCM and is charged with DCM and commercially available diene, 1-methoxy-3-trimethylsilyoxy-1,3-butadiene, followed by the addition of the catalyst, scandium triflate. The suspension is shaken for 12 h and the resin is drained and washed with DMF, MeOH and DCM affording the cycloadduct 38. The resin bound 38 is suspended in 1% HCl in MeOH as above to remove the silyl protecting group to give the vinologous amides 39. Amides of Formula III may be cleaved from resin compounds 39 by exposing them to UV (ca. 360 nm) for 15–180 minutes at 25–50° C. in a suitable solvent such as methanol.

PREPARATION AND USE OF IDENTIFIERS

Identifiers are of the general formula X

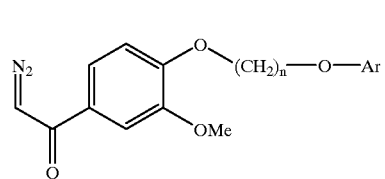

wherein:
n=n=3–12 and Ar is pentachlorophenyl. Eleven compounds of the general formula X were prepared in accordance with the following illustrative example.

Step 1—1-hydroxy-9-(2,3,4,5,6-pentachlorophenoxy) nonane (1.634 g, 4.0 mmol), methyl vanillate (0.729 g, 4.0 mmol) and triphenylphosphine (1.258 g, 4.8 mmol) were dissolved in 20 mL dry toluene under argon. DEAD (0.76 mL, 0.836 g, 4.8 mmol) was added dropwise and the mixture was stirred at 25° C. for one hour. The solution was concentrated to half volume and purified by flash chromatography, eluting with DCM to yield 1.0 g (1.7 mmol, 43%) of the product as a white crystalline solid.

Step 2—The methyl ester product of step 1 (1.0 g, 1.7 mmol) was dissolved in 50 mL THF, 2 mL water was added, followed by LiOH (1.2 g, 50 mmol). The mixture was stirred at 25° C. for one hour then refluxed for 5 hours. After cooling to 25° C., the mixture was poured onto ethyl acetate (200 mL) and washed with 1 M HCl (3×50 mL), then saturated aqueous NaCl (1×50 mL) and then dried over sodium sulfate. The solvent was removed and the crude acid azeotroped once with toluene. Step 3—The crude material from step 2 was dissolved in 100 mL toluene, and 10 mL (1.63 g, 14 mmol) thionyl chloride was added and the resulting mixture was refluxed fro 90 minutes. The volume of the solution was reduced to approximately 30 mL by distillation, then the remaining toluene was removed by evaporation. The crude acid chloride was dissolved in 20 mL dry DCM and cooled to −70° C. under argon and a solution of approximately 10 mmol diazomethane in 50 mL anhydrous ether was added. The mixture was warmed to room temperature and stirred for 90 minutes. Argon was bubbled through the solution for 10 minutes, then the solvents were removed by evaporation and the crude material was purified by flash chromatography, eluting with 10–20% ethyl acetate in hexane. The diazoketone (0.85 g, 1.4 mmol, 82% yield over three steps) was obtained as a pale yellow solid.

An improvement was made to the final diazomethylation step, whereby the acid chloride was reacted with (trimethylsilyl)-diazomethane and triethylamine to give the identifier, which was then used without further purification. This was a significant improvement over the original reaction with diazomethane, as the identifier was now obtained in high yield with no chloromethylketone by-product. Also, purification by flash chromatography was no longer necessary, which in some cases had resulted in significant acidcatalyzed decomposition of the identifier.

ALTERNATE Step 3—5.7 mL (11.4 mmol, 3.00 eq.) of a 2.0 M solution of (trimethylsilyl)-diazomethane in hexanes was added to a solution of the acyl chloride (3.8 mmol, 1.00 eq.) and 1.85 mL (13.3 mmol, 3.5 eq.) of triethylamine in anhydrous THF/acetonitrile (1:1) at 0° C. under argon. The resulting orange solution was stirred at 0° C. for 2 hours, then at 25° C. for 17 hours. (If a precipitate immediately formed upon addition of the (trimethylsilyl)-diazomethane, DCM was added until the precipitate redissolved.) 250 mL of EtOAc was added and the organic layer was washed with 100 mL each of saturated aqueous $NaHCO_3$ and water, then dried with anhydrous $MgSO_4$. Removal of the volatiles in vacuo produced a yellow crystalline product at 60–100% yield.

In the synthesis of Example 1, the 9 identifiers were used to encode the combinatorial library. In Step 1, pentachlorophenyl identifiers where n=9–12 (abbreviated $C_9Cl_5$, $C_{10}Cl_5$, $C_{11}Cl_5$, and $C_{12}Cl_5$) were used in the following binary encoding scheme: 0001=(n=12), 0010=(n=11), 0100=(n=10) and 1000=(n=9). In Step 2, pentachlorophenyl identifiers where n=4–8 (abbreviated $C_4Cl_5$, $C_5Cl_5$, $C_6Cl_5$, $C_7Cl_5$, and $C_8Cl_5$) were used and encoded as follows: 00001=(n=8), 00010=(n=7), 00100=(n=6), 01000=(n=5), and 10000=(n=4).

Thus, in Step 1, reagent 3 (Table 2-1) is encoded "0011" which represents tagging this choice in the synthesis with the two pentachlorophenyl identifiers where n=11 and 12. Likewise, in Step 2 reagent 14 (Table 2-2) is encoded "01110" which represents tagging this choice in the synthesis with the pentachlorophenyl identifiers where n=5, 6 and 7.

EXAMPLE 1

3255 Compound Library

Step (1). Sequential attachment of Bis-Fmoc lysine, photolabile linker, amino alcohols $R^1$, and encoding (a). Attachment of Bis-Fmoc lysine to TentaGel. TentaGel resin (S-$NH_2$, 12 g, 0.32 mmol/g, 3.84 mmol, 180–220 μm) was suspended in a solution of bis-Fmoc lysine (11.2 mmol, 6.8 g), and HOBt (11.2 mmol, 1.5 g), then treated with DIC (22.4 mmol, 3.6 mL). The suspension was shaken overnight, then drained and washed with DMF (3×150 mL), MeOH (3×150 mL), and $CH_2Cl_2$ (3×150 mL). The resin 3 (Scheme 1) was then apportioned into fifteen reaction vessels.

(b). Encoding of resin 3. For all the encoding steps, when one identifier was incorporated, an amount of reagent equal to 7.5% by mass of the resin to be encoded was used. When two identifier were incorporated in the same step, an amount of reagent equal to 10% by mass of the resin to be encoded was used.

Each of the fifteen batches in Step 1a were encoded prior to the addition of the photo-labile linker and the first combinatorial step, with one or more of the $C_{12}Cl_5$-, $Cl_{11}Cl_5$-, $Cl_{10}Cl_5$- and $C_9Cl_5$ linker-diazoketones to produce the appropriate binary code. Identifiers were incorporated one or two at a time until the required binary code was completed. For example, resin batch 11 (12 g) was suspended in 100 mL of ethyl acetate, a solution of $C_{12}Cl_5$-linker-diazoketone (1.2 g) dissolved in 10 mL methylene chloride was added followed by a solution of $C_{11}Cl_5$-linker-diazoketone (1.2 g) dissolved in 10 mL methylene chloride. After agitation for 1 hr, rhodium trifluoroacetate dimer (10 mL of a 1.5 mg/mL solution in methylene chloride) was added and the resin agitated at 25° C. for a further 16 hr. The resin was then filtered and washed with 120 mL portions of methylene chloride (3×), methanol (3×), methylene chloride (3×) and ethyl acetate (1×). This resin batch was again suspended in 100 mL of ethyl acetate and a solution of $C_9Cl_5$-linker diazoketone (0.9 g) dissolved in 10 mL methylene chloride was added. After agitation for 1 hr, rhodium trifluoroacetate dimer (10 mL of 1.5 mg/mL solution in methylene chloride) was added and the resin was agitated at 25° C. for a further 16 hr. The resin was then filtered and washed with 120 mL portions of methylene chloride (3×), methanol (3×), methylene chloride (3×), then dried 2 hr in vacuo.

(c). Removal of Fmoc and attachment of photolinker. A suspension of tagged resin 3 (12 g) in 1:1 piperidine-DMF was shaken 1.5 hr, then drained and washed with DMF (3×120 mL), MeOH (3×120 mL), $CH_2Cl_2$ (3×120 mL). This resin was suspended in DMF (40 mL), and treated with a pre-incubated (1 hr) solution of 4-bromomethyl-3-nitro benzoic acid (22.3 mmol, 5.8 g), HOBt (22.6 mmol, 3 g), DIC (45.2 mmol, 7 mL) in DMF (60 mL). The suspension was shaken overnight, then drained and washed with DMF (3×120 mL), methanol (3×120 mL), DCM (3×120 mL). This was repeated in tandem for each of the fifteen reaction vessels containing the tagged resin 3.

(d). Amino-alcohol addition. Each of the fifteen batches of resin was reacted with one of the amino alcohols in Table 2-1. For example, a suspension of the resin (6 g) in THF (150 mL) was treated with t-butyldimethylsilyl-phenylalaninol (2.95 g, 9.9 mmol), and shaken overnight. The resin was then drained and washed with THF (2×100 mL). The filtrate was concentrated, the residue was taken up in DCM (100 mL) and washed with saturated aqueous sodium bicarbonate (1×100 mL). The aqueous phase was extracted with DCM (2×40 mL) and the combined organic phase was dried over sodium sulfate and concentrated in vacuo. The residue was then added to a suspension of the same resin in DMF (120 mL) along with lithium iodide (3.7 mmol, 0.5 g). The mixture was shaken for 24 hr, drained and the resin was washed with DMF (3×120 mL), MeOH (3×120 mL), and $CH_2Cl_2$ (3×120 mL). This procedure was repeated in tandem, for each of the 15 amino-alcohol in Table 2-1, then the resin was combined as a suspension in methylene chloride, mixed to homogeneity, filtered and dried overnight in vacuo. The resin was divided into 31 identical batches.

Step (2). Addition of $R^2$ Acid Chlorides

The first twenty seven batches of resin 7 were each reacted with one of the twenty seven acid chlorides derived from the acids in entries 1–27 in Table 2-2, the remaining four vessels were first reacted with the same acid chloride 9, then with hydrazine to remove the chloroacetate protecting group and finally each vessel was reacted with one of the four isocyanates in Table 2-3.

(2a). A suspension of resin (1.67 g) in pyridine (10 mL) was treated with one of the twenty seven acid chlorides shown in Table 2-2 (14.8 mmol). This suspension was shaken overnight, then drained and washed with DMF (3×10 mL), MeOH (3×10 mL), and $CH_2Cl_2$ (3×10 mL). This procedure was carried out in tandem for each of the twenty seven acid chlorides in Table 2-2.

(2b). The four remaining batches of resin (4×1.67 g) were suspended in pyridine (4×10 mL) and reacted with acid chloride 9 (4×7.4 mmol, 4×1.3 mL). The four suspensions were shaken for 1.5 hr, drained and each washed with DMF (3×10 mL), methanol (3×10 mL) and DCM (3×10 mL). The four batches of resin (1.67 g) were shaken 1 hr in a 10% hydrazine-methanol (4×10 mL) solution, then drained and each washed with DMF (3×10 mL), methanol (3×10 mL) and DCM (3×10 mL). Each batch of resin was treated with one of the isocyanates in table 2-3. To a suspension of the resin (1.67 g) in acetonitrile (10 mL) was added the isocyanate (14.8 mmol) along with a catalytic amount of DBU (30 µL). The mixture was shaken overnight, drained and the resin was washed with DMF (3×10 mL), methanol (3×10 mL) and DCM (3×10 mL). This last procedure was carried out in tandem for each of the four isocyanates in Table 2-3.

Encoding of Step (2)

Each of the thirty-one resin batches in Step (2) was encoded with one or more of the $C_8Cl_5$-, and $C_4Cl_5$-linker-diazoketones to produce the appropriate binary code. Identifiers were incorporated one or two at a time until the required binary code was completed. For example, resin batch 13 (1.67 g) was suspended in 50 mL of ethyl acetate, a solution of $C_8Cl_5$-linker-diazoketone (0.13 g) dissolved in 5 mL methylene chloride was added. After agitation for 1 hr, rhodium trifluoroacetate dimer (3.3 mL of a 1.5 mg/ML solution in methylene chloride) was added and the resin agitated at 25° C. for a further 16 hr. The resin was then filtered and washed with 50 mL portions of methylene chloride (3×), methanol (3×), methylene chloride (3×) and ethyl acetate (1×). This resin batch was suspended in 50 mL of DCM and a solution of $C_6Cl_5$-linker diazoketone (0.18 g) dissolved in 5 mL methylene chloride was added followed by a solution of $C_5Cl_5$-linker-diazoketone (0.18 g) dissolved in 5 mL methylene chloride. After agitation for 1 hr, rhodium trifluoroacetate dimer (3.3 mL of 1.5 mg/mL solution in methylene chloride) was added and the resin was agitated at 25° C. for a further 16 hr. The resin was then filtered and washed with 120 mL portions of methylene chloride (3×), methanol (3×), methylene chloride (3×).

After encoding, the thirty-one batches were combined as a suspension in methylene chloride, mixed to homogeneity, filtered, and dried in vacuo.

Step (3). Conversion to the Aldehyde (a). The resin (10 g) was suspended in a 1% solution (by volume) of concentrated HCl in methanol (150 mL). The mixture was shaken for 7 hr, drained and the resin was washed with methanol (1×150 mL), DMF (3×150 mL), methanol (3×150 mL), DCM (3×150 mL).

(b) The resin (10 g) was suspended in DMSO (130 mL) and a solution of IBX in DMSO (22.3 mmol, 20 mL of a 0.31 g/mL solution) was added. The mixture was shaken overnight, drained and the resin was washed with DMSO (130 mL). The resin (10 g) was suspended in DMSO again and another solution of IBX (22.3 mmol, 20 mL of a 0.31 g/mL solution) was added. The mixture was shaken for 4 hr, drained, and the resin was washed with DMSO (3×150 mL), methanol (3×150 mL), DCM (3×150 mL). The resin was dried overnight in vacuo.

The dried resin 14 was divided into several portions. One portion of resin (3.5 g) was taken to the next step in this Example 1. The remaining portions were used to prepare the libraries of examples 3, 5, 7, 9, 11 and 13.

Step (4) Addition of Phosphites

The resin was divided into 7 reaction vessels so that each vessel contained 0.35 grams of resin. Each vessel was reacted with one of the phosphites shown in Table 2-4. For example, to the resin (0.35 g) suspended in DCM (10 mL) was added one of the phosphites (3.2 mmol) followed by triethylamine (3.2 mmol). The mixture was shaken for 18 hr, then drained and the resin was washed with DMF (3×10 mL), methanol (3×10 mL), DCM (3×10 mL) and dried overnight in vacuo. This procedure was carried out in tandem for each of the seven phosphites in Table 2-4. Each of these final resin batch was individually stored as a separate sub-library, obviating any encoding for Step 4.

EXAMPLE 2

Verification of Synthesis

Several members from the library of Example 1 were synthesized on the solid phase to confirm the validity of the synthetic route and the identity of the final products. The compounds were cleaved from the resin via photoelution at 50° C. for 3–4 hr at 353 nm and the structures were confirmed by spectroscopic methods.

EXAMPLE 3

23250 Member Library

Step (1). Elaboration of the Hydroxystatine Motif (a). The resin aldehyde 14 from step (3), Example 1, (10 g) was suspended in THF and (t-butoxycarbonylmethylene)-triphenylphosphorane (22.5 mmol, 8.4 g) was added. The mixture was shaken overnight, drained and the resin was washed with THF (3×150 mL), methanol (3×150 mL) and DCM (3×150 mL).

(b). The resin (10 g) was then suspended in a 1:1 mixture of acetone-water (150 mL) and NMO (17.9 mmol, 2.1 g) was added along with a solution of osmium tetroxide in water (0.9 mmol, 5.7 mL of a 4% (weight) solution). The mixture was shaken overnight, drained and the resin was washed with water (3×150 mL), pyridine (3×150 mL), DMF (3×150 mL), methanol (3×150 mL), DCM (3×150 mL).

(c). The resin (10 g) was subsequently suspended in pyridine (90 mL) and acetic anhydride (60 mL) was added along with a catalytic amount of DMAP. The mixture was shaken overnight, drained and washed with DMF (3×150 mL), methanol (3×150 mL), DCM (3×150 mL) and dried 5 hr in vacuo.

Step (2): Hydrolysis of Ester, Amide Bond Formation and Deprotection of Diol (a). The resin was divided into 50 reaction vessels so that each vessel contained 0.47 grams of resin. In all 50 vessels, the resin (0.47 g) was suspended in TFA, shaken 2 hr and the mixture was drained. The resin was washed with DMF (3×10 mL), methanol (3×10 mL), DCM (3×10 mL). In all 50 vessels, the resin (0.47 g) was suspended in DMF (1 mL), pyridine (1 mL), pentafluorophenol (500 mg) and pentafluorophenyl trifluoroacetate (1 mL) were added. The mixture was shaken 1 hr, then drained and the resin was rinsed with DMF (2×10 mL). In all 50 vessels, the resin (0.46 g) was suspended in DMF (10 mL), and to each vessel was added one of the amines in Table 2-5 (4.2 mmol). The mixture was shaken overnight, drained and the resin was washed with DMF (3×10 mL), methanol (3×10 mL) and DCM (3×10 mL). This procedure was carried out in tandem for each of the 50 amines in Table 2-5. In all 50 flasks, the resin was then suspended in a 10% solution of hydrazine in methanol (10 mL), shaken for 2 hr, drained and washed with methanol (10 mL), DMF (3×10 mL), methanol (3×10 mL), DMF (3×10 mL). Each of these final resin batches was individually dried and stored as a separate sub-library obviating any encoding for Step (2).

EXAMPLE 4

Verification of Synthesis

Several members from the library of Example 3 were synthesized on the solid phase to confirm the validity of the synthetic route and the identity of the final products. The compounds were cleaved from the resin via photoelution at 50° C. for 3–4 hr at 353 nm and the structures were confirmed by spectroscopic methods.

EXAMPLE 5

465 Compound Library

Resin 14 (100 mg, 0.5 mmol), indium metal (50 mg, 0.44 mmol), THF (2 mL), water (2 mL) and allyl bromide (60 mL, 0.69 mmol) were combined in a reaction vessel and sonicated in a ultrasonic cleaning bath. After approximately 6 hr of sonication, a milky white precipitate formed and the pH of heterogenous solution was three. Soncation was continued for another 3 hr. The resin was then drained and washed with water (10 mL), THF (3×10 mL), and DCM. It was then dried in vacuo at room temperature.

EXAMPLE 6

Verification of Synthesis

A member from this library was synthesized on the solid phase to confirm the validity of the synthetic route and the identity of the final product. The compound was cleaved from the resin via photoelution at 50° C. for 3–4 hr at 353 nm and the structures were confirmed by spectroscopic methods.

EXAMPLE 7

465 Compound Library

The resin (100 mg), acetone (2 mL), water (2 mL) and 4-methylmorpholine-N-oxide (NMO, 33 mg, 0.28 mmol) were combined and shaken for 5 minutes until the NMO was completely dissolved. To the resulting suspension of resin was added an aqueous solution of $OsO_4$ (4% $OsO_4$ by wt., 60 μL, 20 mol %) which immediately caused the resin to darken in color. The resin was shaken overnight then washed with water, DMF, MeOH, and $CH_2Cl_2$. It was then dried in vacuo at room temperature.

EXAMPLE 8

Verification of Synthesis

A member from this library was synthesized on the solid phase to confirm the validity of the synthetic route and the identity of the final product. The compound was cleaved from the resin via photoelution at 50° C. for 3–4 hr at 353 nm and the structures were confirmed by spectroscopic methods.

EXAMPLE 9

465 Compound Library

The resin (100 mg) was treated with saturated aqueous solution of $NaIO_4$ (5 mL; 150 mg/mL) for 5 minutes; after draining off the solution the treatment was repeated in this manner three additional times. The resin was then washed with water, MeOH, and $CH_2Cl_2$. The vacuum-dried resin (100 mg) was shaken at room temperature with a 2 M solution of $LiBH_4$ in THF (2 mL, 77 equiv.) for 20 minutes. The resin was then washed with THF, MeOH, and $CH_2Cl_2$. It was then dried in vacuo at room temperature.

EXAMPLE 10

Verfication of Synthesis

A member from this library was synthesized on the solid phase to confirm the validity of the synthetic route and the identity of the final product. The compound was cleaved from the resin via photoelution at 50° C. for 3–4 hr at 353 nm and the structures were confirmed by spectroscopic methods.

EXAMPLE 11

24180 Compound Library

A flask was charged with vacuum-dried resin (10 g) and $CH_2Cl_2$ (400 mL) then cooled to 0° C. for 30 minutes. To this stirred solution was added 2,6-lutidine (4 mL, 34 mmol, 7 equiv.), followed by tert-butyldimethylsilyl trifluoromethanesulfonate (5 equiv.). After 5 minutes of stirring the ice bath was removed and the reaction was allowed to stir for an additional 1.25 hours at room temperature. The resin was then isolated by filtration and washed with alternating portions of MeOH and $CH_2Cl_2$.

The resin was then treated with saturated aqueous solution of $NaIO_4$ (500 mL; 150 mg/mL) for 5 minutes; after draining off the solution the treatment was repeated in this manner three additional times. The resin was then washed with water, MeOH, and $CH_2Cl_2$.

A 1 g sample of vacuum-dried resin was shaken at room temperature with a 2 M solution of $LiBH_4$ in THF (77 equiv.) for 20 minutes. The resin was then washed with THF, MeOH, and $CH_2Cl_2$. It was then dried in vacuo at room temperature. It was divided into two portions and each portion was treated with either phenyl isocyanate or butyl isocyanate (by shaking overnight with the isocyanate (35 equiv.) in $CH_3CN$). The resin batches were washed with methanol, DCM and 1% HCl/MeOH (50 mL each) for 15minutes, then the solvent was drained off and it was recharged with 1% HCl/MeOH a second time. After 4.5 hours of shaking the resin was washed with MeOH and CH$_2$Cl$_2$ to give the corresponding carbamates.

Four hundred mg of resin, 10 mL of trimethyl orthoformate and 50 equiv. of methylamine were shaken for 15 minutes. The resin was then washed four times with 5% acetic acid in MeOH before being charged with 5% AcOH/ MeOH (7 mL) and methylamine (50 equiv.). After 5 minutes of shaking solid sodium cyanoborohydride (300 mg, 24 equiv.) was added and the mixture was shaken overnight. The resin was then washed with MeOH, 1:1 MeOH/water, water, aqueous K$_2$CO$_3$, and water, 1:1 MeOH/water, and MeOH. The resin was washed with 1% HCl/MeOH for 15 minutes, then the solvent was drained off and it was recharged with 1% HCl/MeOH a second time. After 4.5 hours of shaking the resin was washed with MeOH and CH$_2$Cl$_2$. and dried in vacuo.

The reaction was carried out in tandem for each of the primary and secondary amines in Table 2-7 and 2-8. In the case of the primary amines of Table 2-7 further derivatization was possible (prior to desilylation) through acylation (20 equiv. of acylating reagent), sulfonylation (20 equiv. of sulfonyl chloride reagent), ureidonation (30 equiv. of isocyanate in acetonitrile), or reductive amination with an aldehyde (20 equiv.) to give the desired derivative using conditions as described above as per the reagents in Table 2-9, 2-10, and 2-11.

EXAMPLE 12

Verfication of Synthesis

Several members from this library were synthesized on the solid phase to confirm the validity of the synthetic route and the identity of the final products. The compound was cleaved from the resin via photoelution at 50° C. for 3–4 hr at 353 nm and the structures were confirmed by spectroscopic methods.

EXAMPLE 13

465 Compound Library

The resin (100 mg), trimethyl orthoformate (7 mL) and benzylamine (50 equiv.) were shaken for 15 minutes. The resin was then washed three times with CH$_2$Cl$_2$, then charged with CH$_2$Cl$_2$ (15 mL), 1-methoxy-3-(trimethylsiloxy)-1,3-butadiene (80 μL, 0.2 mmol, 7 equiv.) and scandium(III)trifluoromethanesulfonate (10 mg, 0.01 mmol, 33 mol %) and shaken overnight. The resin was then drained and washed with DMF, MeOH, and CH$_2$Cl$_2$. The resin was washed with 1% HCl/MeOH (10 mL) for 15 minutes, then the solvent was drained off and it was recharged with 1% HCl/MeOH (10 mL) a second time. After 4.5 hours of shaking the resin was washed with MeOH and CH$_2$Cl$_2$. and dried in vacuo.

EXAMPLE 14

Verification of Synthesis

A member from this library was synthesized on the solid phase to confirm the validity of the synthetic route and the identity of the final product. The compound was cleaved from the resin via photoelution at 50° C. for 3–4 hr at 353 nm and the structures were confirmed by spectroscopic methods.

EXAMPLE 15

Decoding Procedure

A bead is placed in a 1.3 mm diameter pyrex capillary with 2 μL of acetonitrile. Ceric ammonium nitrate solution (2 μL of a 0.1 M aq. solution) and hexane (3 μL) are added and the two-phase mixture centrifuged briefly. The tube is sealed and left at 35° C. for 16 hr, then opened. The organic layer is removed by syringe and mixed with 1 μL of N,O-bis(trimethylsilyl)acetamide. The silated tag solution (1 μL) is analyzed by GC with electron capture (EC) detection.

The GC analysis is performed with a Hewlett Packard 5890 plus gas chromatograph. On column injection into a 5 m, 0.32 mm retention gap connected to a 25 m, 0.2 mm crosslinked 5% phenylmethyl silicone column is used. The temperature and pressure programs for the analysis are 200–320° C., 15° C./min., then 320° C. for 10 min. and 20–40 psi at 2 psi/min, then 40 psi for 10 min. The EC detector is maintained at 400° C. and the auxiliary gas is set at 35 psi.

The identity of the library compound attached to the bead is ascertained based on the reagents utilized in the synthesis of such compound, which are readily determined from the binary codes associated, respectively, with each of the identifiers for such reagents, as characterized through the above procedure. The binary codes for the identifiers assigned to the various reagents are represented in the following tables.

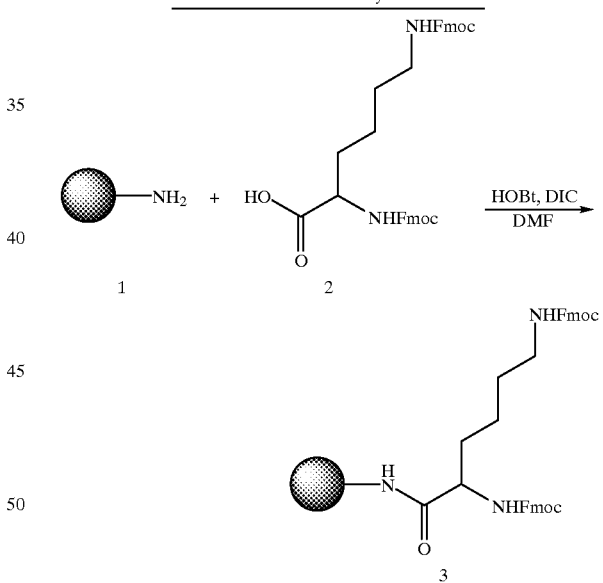

Scheme 1
Attachment of bis-Fmoc Lysine to Resin

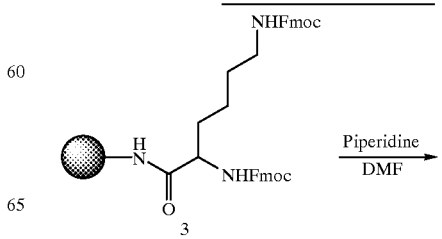

Scheme 2
Attachment of BNB Linker

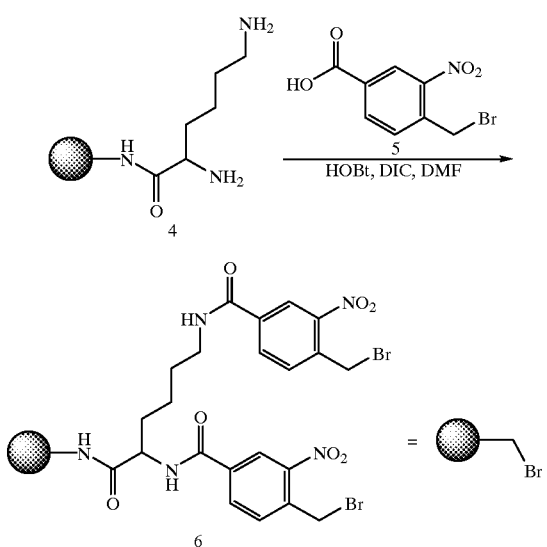
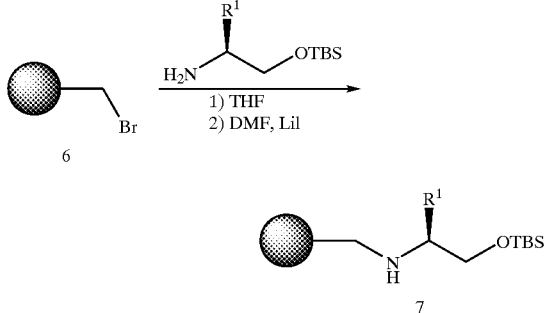
Scheme 3
Attachment of Amino Alcohols (R¹)
(See Table 2-1 for a selection of R¹ amino alcohols)
Scheme 4
Attachment of Acid Chlorides (R²)
Scheme 4a:
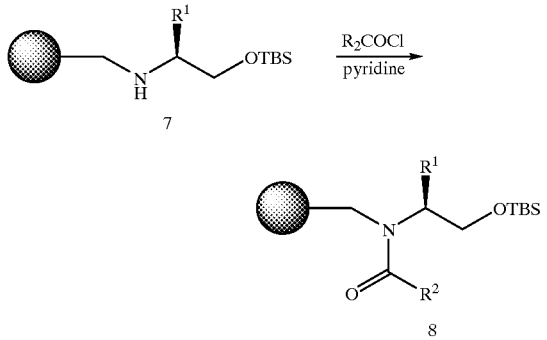
(See Table 2-2 for a selection of R² acid chlorides)
Scheme 4b:
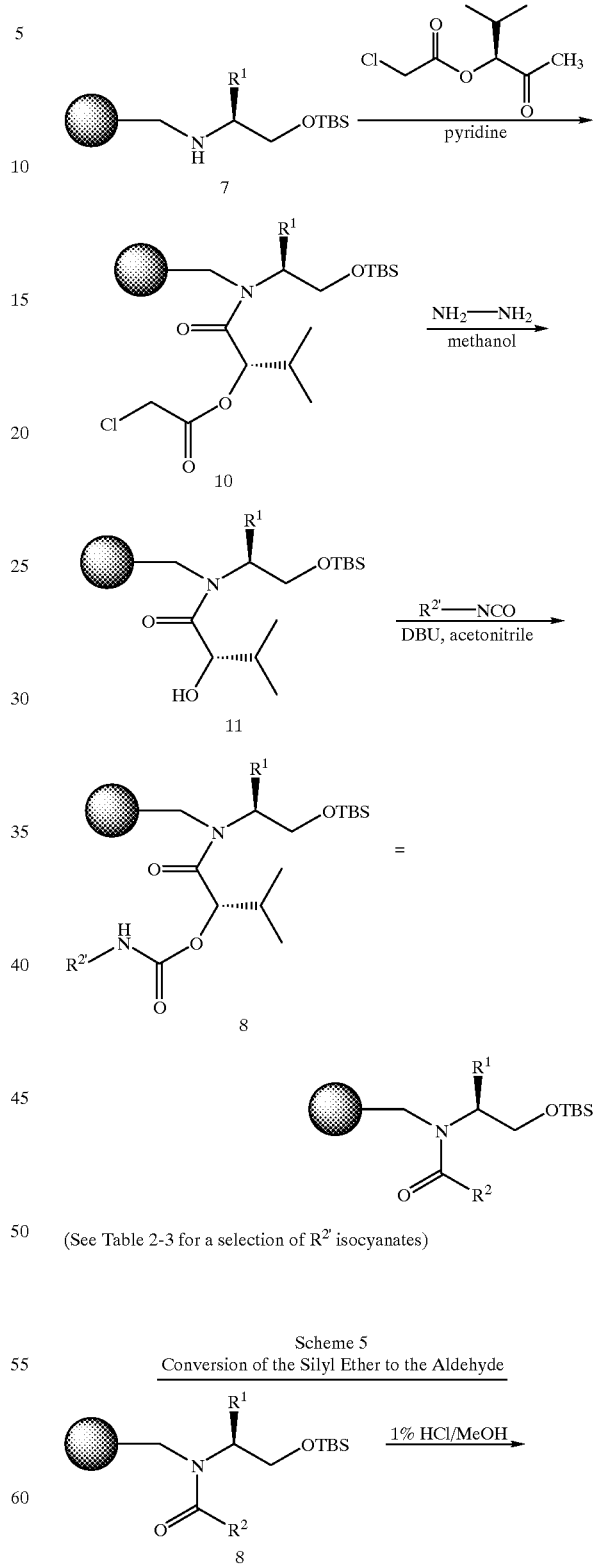
(See Table 2-3 for a selection of R²′ isocyanates)
Scheme 5
Conversion of the Silyl Ether to the Aldehyde

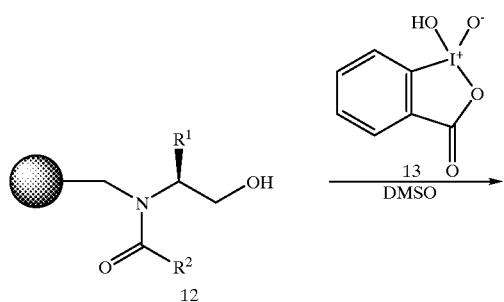
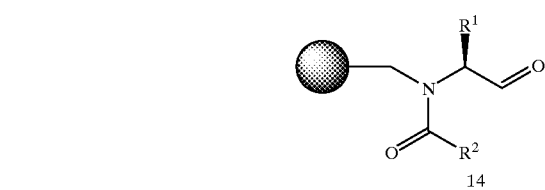
Scheme 6
Addition of Phosphites
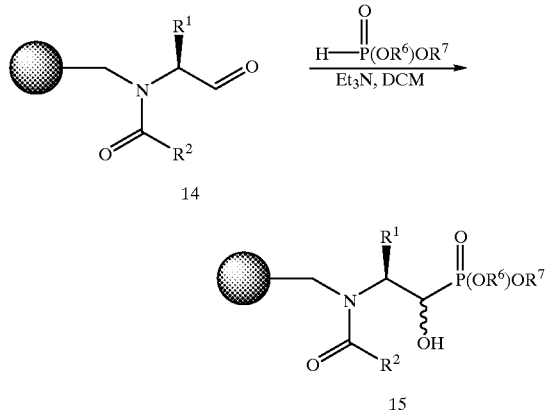
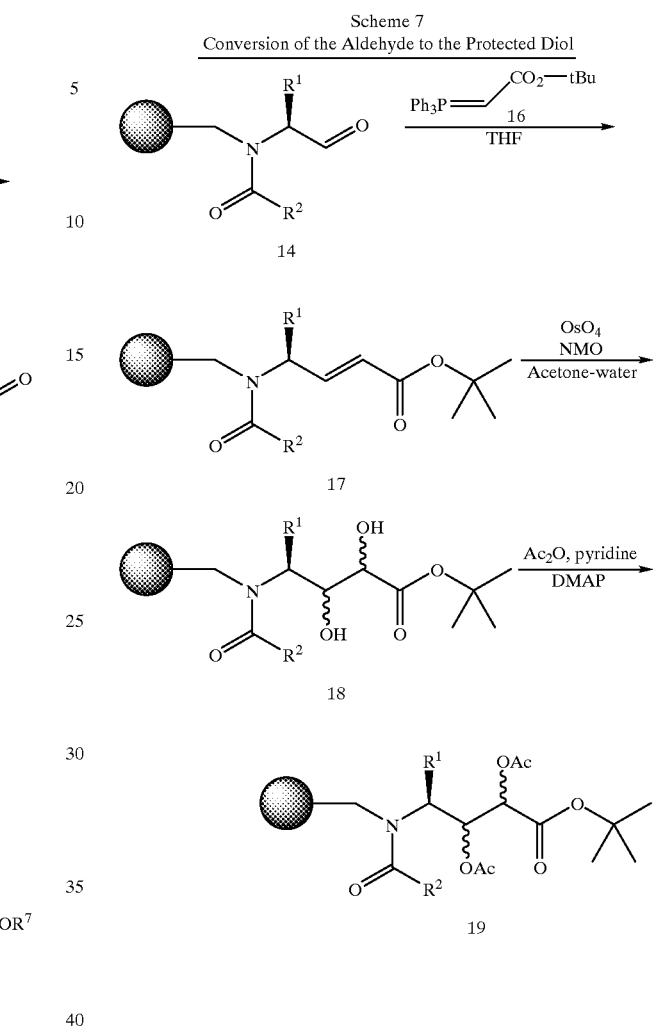

Scheme 8
Hydrolysis of t-Butyl Ester, Activation and Coupling of Acid with Amines and Deprotection of Diol.
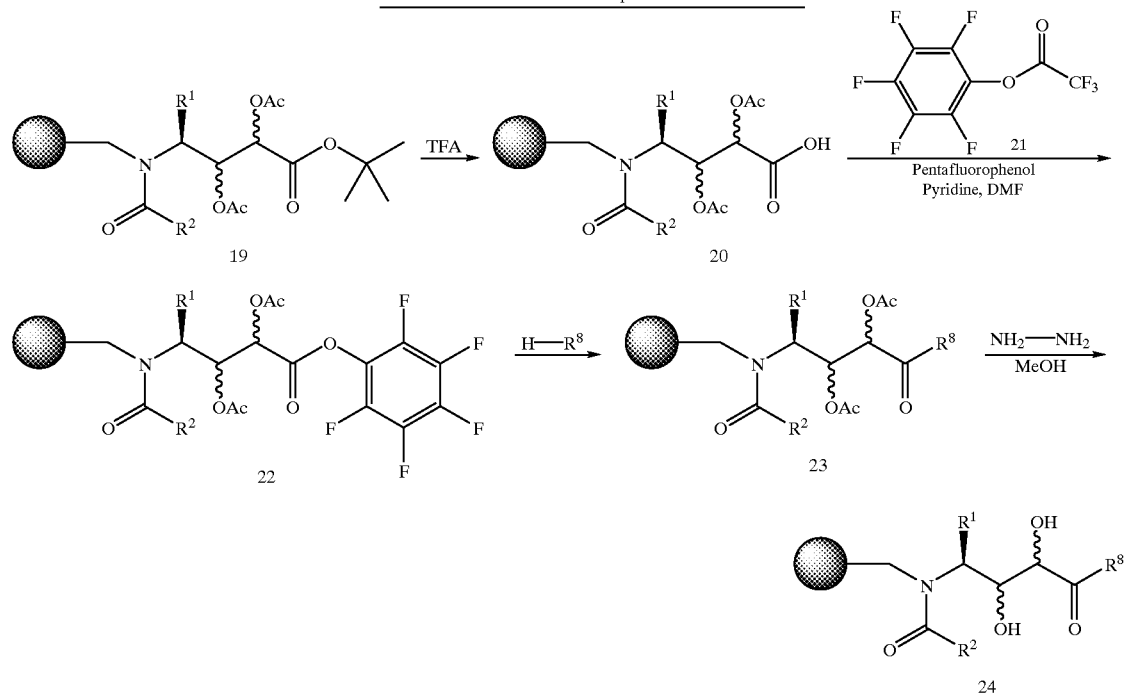
Scheme 9
Addition of Allyl bromide
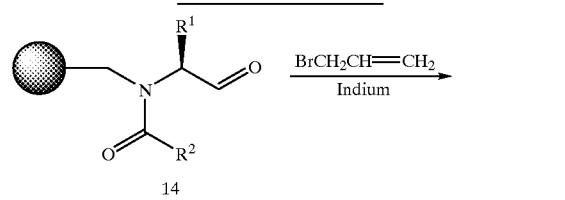
Scheme 10
Osmylation reaction
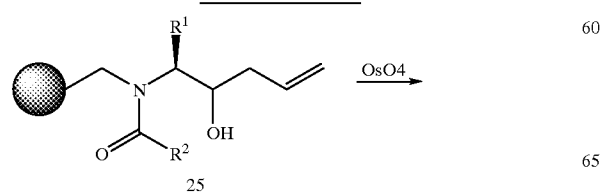
-continued
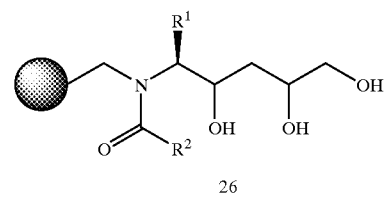
Scheme 11
Periodate Cleavage and Reduction
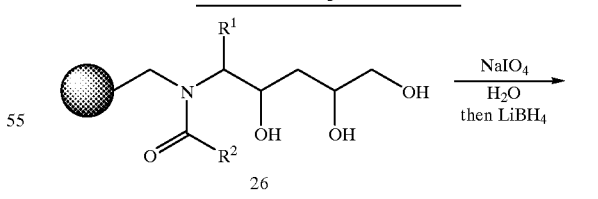
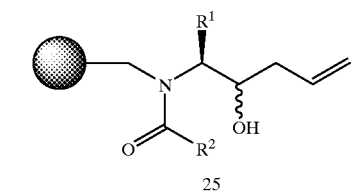

Scheme 12
Protection, Oxidation and Reductive Amination
and Derivatization
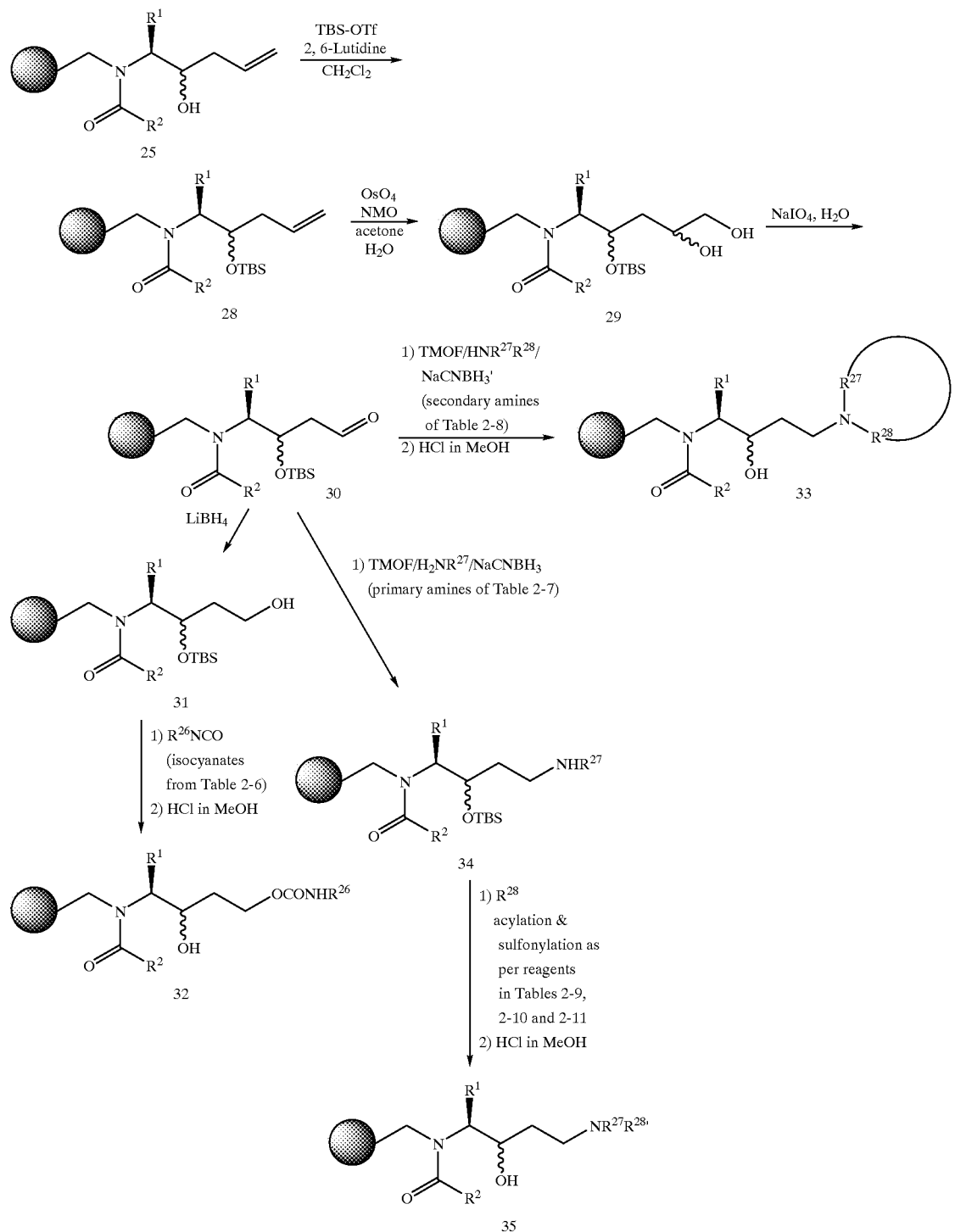

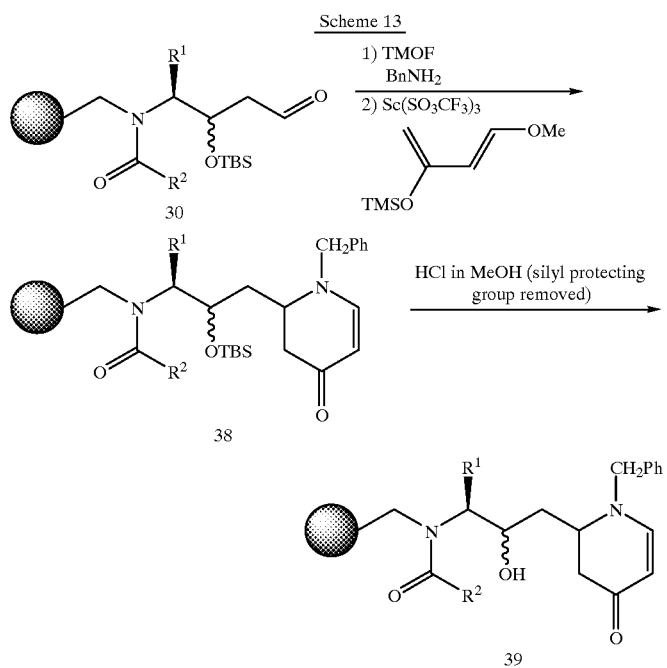

Scheme 13

| TABLE 1 | | | TABLE 1-continued | |
|---|---|---|---|---|
| Linker Groups | | | Linker Groups | |
| Linker Group, -L'- | Cleavage reagent | | Linker Group, -L'- | Cleavage reagent |
| 1. [2-nitrobenzyl-B] | light | | 6. [phenyl-O-CH₂-B ether] | $H_3O^+$ |
| 2. [2-nitrobenzyl carbonate-B] | light | | 7. [2-methoxy phenyl-O-CH₂-B] | $H_3O^+$ |
| 3. [2-nitro-α-substituted benzyl-B] | light | | 8. [furan-B] | 1) $O_2$ or $Br_2$, MeOH  2) $H_3O^+$ |
| 4. [RO-aryl-B] | $Ce(NH_4)_2(NO_3)_6$ | | 9. —CH=CH(CH₂)₂— | $O_3$, $OsO_4/IO_4^-$, or $KMnO_4$ |
| 5. [2-bromo-aryl-B] | Li, Mg, or BuLi | | 10. —CH=CHCH₂— | $O_3$, $OsO_4/IO_4^-$, or $KMnO_4$ |
| | | | 11. —CH₂CH=CH— | $O_3$, $OsO_4/IO_4^-$, or $KMnO_4$ |
| | | | 12. —CH=CHCH₂B— | $(Ph_3)PRhCl(H)$ |
| | | | 13. —S—CH₂—B— | $Hg^{+2}$ |

TABLE 1-continued

Linker Groups

| Linker Group, -L'- | Cleavage reagent |
|---|---|
| 14. [structure with X, B] | Zn or Mg |
| 15. [structure with OH, B] | Oxidation, e.g., Pb(OAc)$_4$ or H$_5$IO$_6$ |

R = H or lower alkyl; B = O or NH; and
X = electron withdrawing group such as Br, Cl, and I.

∫ = point of attachment to (C(O)

TABLE 2-1

Amino Alcohol Reagents (R$^1$) and Encoding Scheme

| | Amino Alcohol Reagent | Binary Code |
|---|---|---|
| 1. | [benzyl, H$_2$N, OTBS] | 0001 |
| 2. | [butyl chain, H$_2$N, OTBS] | 0010 |
| 3. | [isobutyl, H$_2$N, OTBS] | 0011 |
| 4. | [methyl, H$_2$N, OTBS] | 0100 |
| 5. | [isopropyl, H$_2$N, OTBS] | 0101 |
| 6. | [4-OMe-benzyl, H$_2$N, OTBS] | 0110 |
| 7. | [4-Cl-benzyl, H$_2$N, OTBS] | 0111 |
| 8. | [3,4-diCl-benzyl, H$_2$N, OTBS] | 1000 |
| 9. | [phenyl, H$_2$N, OTBS] | 1001 |
| 10. | [phenethyl, H$_2$N, OTBS] | 1010 |
| 11. | [diphenyl, H$_2$N, OTBS] | 1011 |
| 12. | [biphenyl-CH$_2$, H$_2$N, OTBS] | 1100 |
| 13. | [naphthyl-CH$_2$, H$_2$N, OTBS] | 1101 |

TABLE 2-1-continued
Amino Alcohol Reagents (R¹) and Encoding Scheme
| Amino Alcohol Reagent | Binary Code |
|---|---|
| 14. 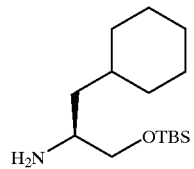 | 1110 |
| 15. 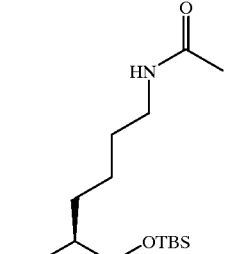 | 1111 |
TABLE 2-2
Acid Reagents (R²) and Encoding Scheme
| Acid Reagent | Binary Code |
|---|---|
| 1. 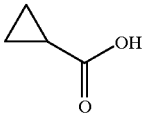 | 00001 |
| 2. 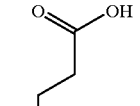 | 00010 |
| 3.  | 00011 |
| 4. 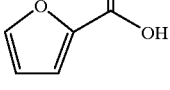 | 00100 |
| 5. 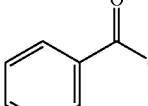 | 00101 |
TABLE 2-2-continued
Acid Reagents (R²) and Encoding Scheme
| Acid Reagent | Binary Code |
|---|---|
| 6. 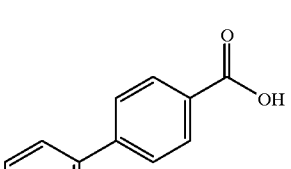 | 00110 |
| 7. 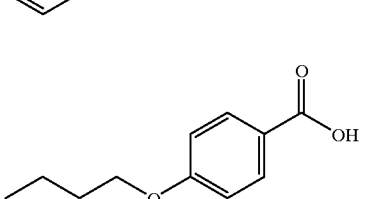 | 00111 |
| 8. 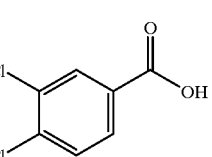 | 01000 |
| 9. 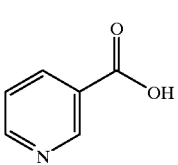 | 01001 |
| 10. 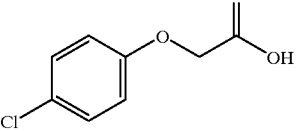 | 01010 |
| 11. 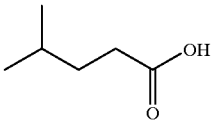 | 01011 |
| 12. 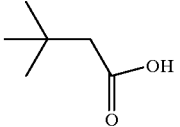 | 01100 |
| 13. 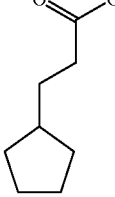 | 01101 |

TABLE 2-2-continued

Acid Reagents (R²) and Encoding Scheme

| | Acid Reagent | Binary Code |
|---|---|---|
| 14. | 2,3-difluorobenzoic acid | 01110 |
| 15. | 2-fluoro-4-(trifluoromethyl)benzoic acid | 01111 |
| 16. | 2,4-dimethoxybenzoic acid | 10000 |
| 17. | quinoline-3-carboxylic acid | 10001 |
| 18. | 4-phenoxybenzoic acid | 10010 |
| 19. | 1-naphthoic acid | 10011 |
| 20. | 3,3-diphenylpropanoic acid | 10100 |
| 21. | N-Cbz-proline | 10101 |
| 22. | 4-phenylbutanoic acid | 10110 |
| 23. | 3-[4-(2-methoxyethoxy)phenyl]propanoic acid | 10111 |
| 24. | 2-indanylacetic acid | 11000 |
| 25. | 4-(3,4-dimethoxyphenyl)butanoic acid | 11001 |
| 26. | (2,6-dimethylphenoxy)acetic acid | 11010 |
| 27. | (2-naphthyloxy)acetic acid | 11011 |
| 28. | Bu-NH-C(O)-O-CH(iPr)-COOH | 11100 |
| 29. | 4-(PhO)Ph-NH-C(O)-O-CH(iPr)-COOH | 11101 |
| 30. | Ph-NH-C(O)-O-CH(iPr)-COOH | 11110 |

TABLE 2-2-continued

Acid Reagents (R²) and Encoding Scheme

| Acid Reagent | Binary Code |
|---|---|
| 31. Ph(CH₂)₂-NH-C(O)-O-CH(iPr)-COOH | 11111 |

TABLE 2-3

Isocyanate Reagents (R²')

Isocyanate Reagent 1. butyl-NCO
2. 4-phenoxyphenyl-NCO
3. phenyl-NCO

TABLE 2-3-continued

Isocyanate Reagents (R²')

Isocyanate Reagent 4. phenethyl-NCO

TABLE 2-4

Phosphite Reagents
Y = —P(O)(OR⁶)OR⁷

1. H-P(O)(OMe)₂
2. H-P(O)(OEt)₂
3. H-P(O)(OBu)₂
4. H-P(O)(OCH₂Ph)₂
5. H-P(O)(OCH₂CF₃)₂
6. H-P(O)(OCH₂CH₂Cl)₂
7. cyclic H-P(O)(OCH₂CH₂O)

TABLE 2-5

Amine Reagents (R⁸)

1. H₂N-butyl
2. 1-adamantyl-CH₂-NH₂

TABLE 2-5-continued

Amine Reagents (R⁸)

TABLE 2-5-continued
Amine Reagents (R⁸)
22. 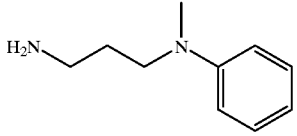
23. 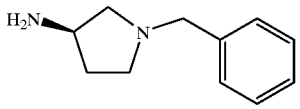
24. 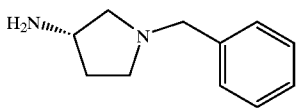
25. 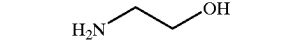
26. 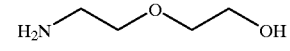
27. 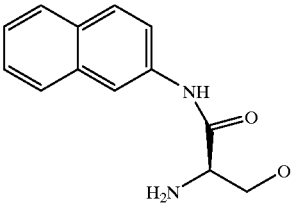
28. 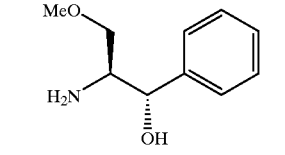
29. 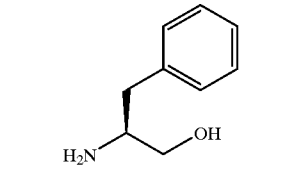
30. 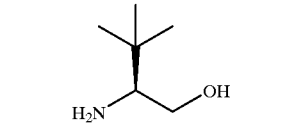
31. 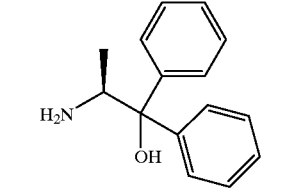
32. 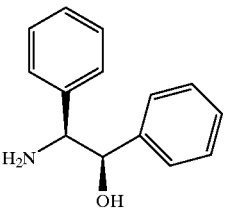
33. 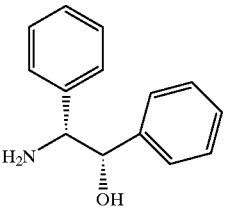
34. 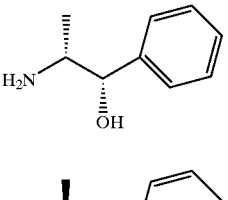
35. 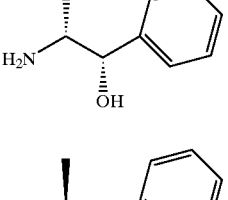
36. 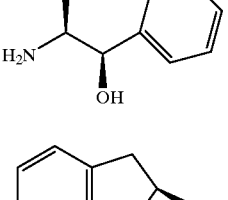
37. 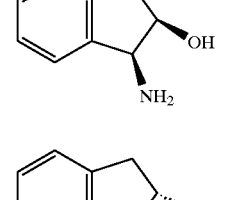
38. 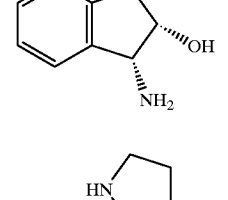
39. 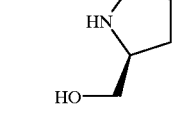
40. 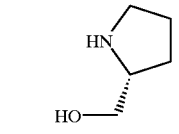

TABLE 2-5-continued

Amine Reagents (R⁸)

41. [structure: (S)-2-(methoxymethyl)pyrrolidine, HN-pyrrolidine with CH₂-OMe]

42. [structure: 2-amino-3-methylpentan-1-ol, H₂N-CH(sec-Bu)-CH₂OH]

43. [structure: piperazine with furan-2-carbonyl group, HN-piperazine-C(=O)-furan]

44. [structure: threoninamide, H₂N-CH(CH(OH)CH₃)-C(=O)NH₂]

45. [structure: 1-(3-aminopropyl)-2-pyrrolidinone, H₂N-CH₂CH₂CH₂-N(pyrrolidinone)]

46. [structure: Ala-Leu-NH₂ dipeptide amide]

47. [structure: H₂N-CH(CH₃)-C(=O)-NHBu, alaninamide N-butyl]

48. [structure: (S)-prolinamide, HN-pyrrolidine-CONH₂]

49. [structure: 4-(aminomethyl)benzenesulfonamide, H₂N-CH₂-C₆H₄-SO₂NH₂]

50. [structure: N-(2-aminoethyl)-4-methylbenzenesulfonamide, tosyl-NH-CH₂CH₂-NH₂]

TABLE 2-6

Isocyanate Reagents R²⁶NCO

Isocyanate Reagent

1. [structure: n-butyl isocyanate]

2. [structure: phenyl isocyanate]

TABLE 2-7

Primary Amine Reagents R²⁷NH₂

1. MeNH₂
2. H₂N-CH₂CH₂CH₂CH₃ (n-butylamine)
3. H₂N-CH₂CH₂-OMe (2-methoxyethylamine)
4. H₂N-CH(CH₃)₂ (isopropylamine)
5. H₂N-CH₂-C₆H₅ (benzylamine)
6. H₂N-indanyl (1-aminoindane) (racemic)

TABLE 2-7-continued
Primary Amine Reagents R²⁷NH₂
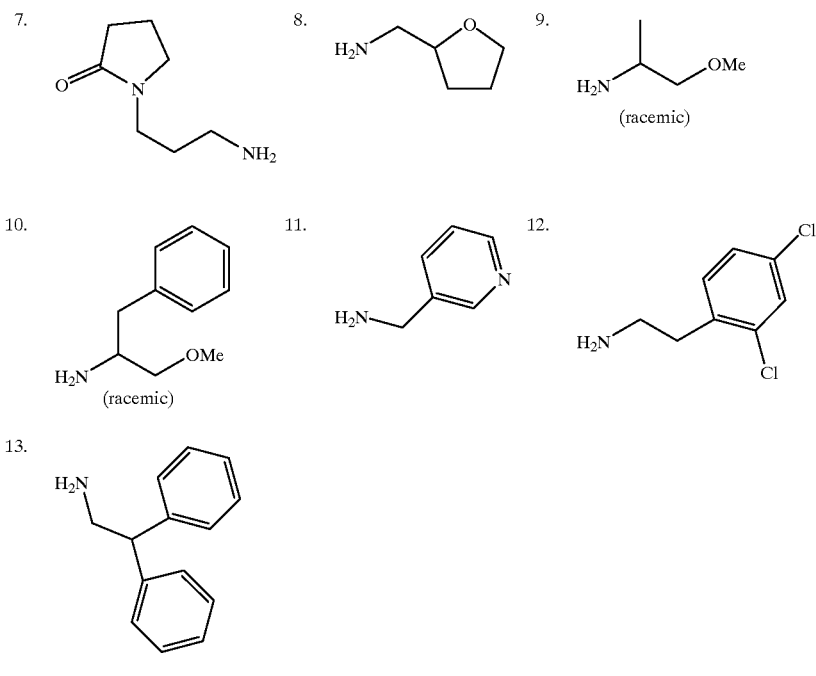
TABLE 2-8
Secondary Amine Reagents HNR²⁷R²⁸
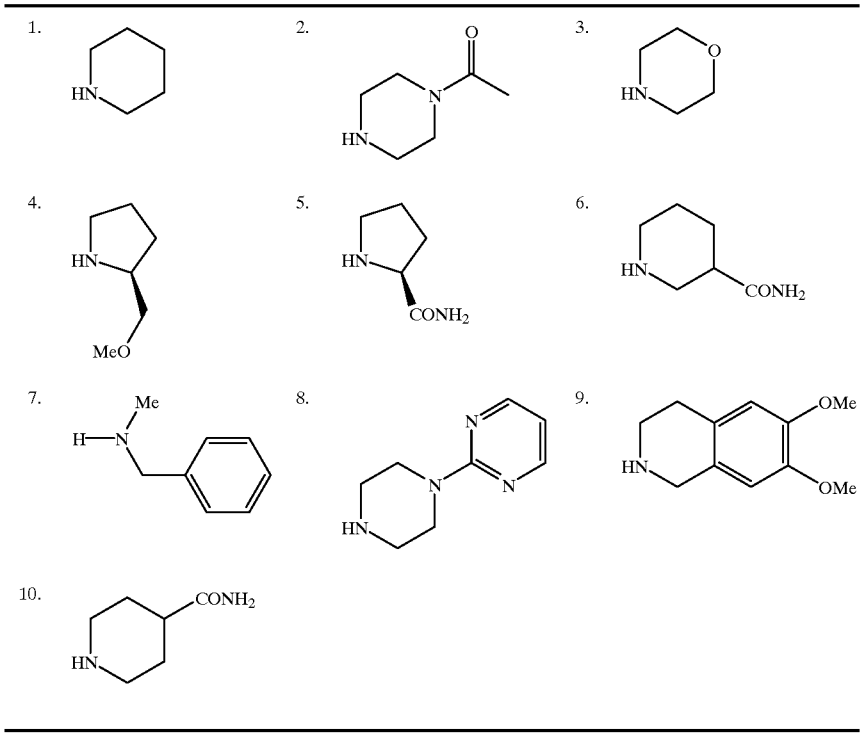

TABLE 2-9

List of reagents used to provide $R^{28}$ when $R^{27}$ was $CH_3$ (Amine 1 from Table 2-7)

A. Acylating and sulfonylating reagents

[Structures: acetic anhydride; benzoyl chloride; hexanoyl chloride; phenoxyacetyl chloride; Cl—SO$_2$Me; Cl—SO$_2$Ph]

B. Aldehydes for reductive amination

[Structures: OHC-CH$_2$CH$_2$-S-CH$_3$; 4-phenoxybenzaldehyde]

C. Isocyanates for urea formation

[Structures: OCN-CH$_2$CH$_2$-Ph; OCN-butyl]

TABLE 2-10

List of reagents used to provide $R^{28}$ when the Amines 2 to 4 in table 2-7 were used in the Reductive Amination

[Structures: 1. acetic anhydride; 2. Cl—SO$_2$Me; 3. benzoyl chloride (Cl-C(O)-Ph); 4. Cl—SO$_2$Ph]

TABLE 2-11

List of reagents used to provide $R^{28}$ when Amines 5–13 in table 2-7 were used in the Reductive Amination

[Structures: 1. acetic anhydride; 2. Cl—SO$_2$Me]

What is claimed is:

1. A combinatorial chemical library comprising a plurality of members of the Formula I:

(T-L)q-[S]-C(O)-L'-Z    I wherein:

[S] is a solid support;

T-L- is an identifier residue;

-L'-Z is a linker/compound residue;

q is 0–30; and

Z is

[Structure showing: N with R$^1$ substituent, N-methyl, N-C(O)R$^2$, CH-Y, CH-OH]

wherein $R^1$ is chosen from $C_1$ to $C_{20}$ hydrocarbon, substituted aryl, substituted aralkyl and $(CH_2)_n NHC(O)R^3$;

$R^2$ is chosen from $C_1$ to $C_{20}$ hydrocarbon, substituted alkyl, substituted aryl, heteroaryl, aryloxyalkyl, alkoxyalkyl, and —CH(R$^4$)OC(O)NHR$^3$;

$R^3$ is chosen from $C_1$ to $C_{20}$ hydrocarbon and substituted aryl;

$R^4$ and $R^5$ independently are lower alkyl or aryl;

n is 1–4;

Y is chosen from —P(O)(OR$^6$)(OR$^7$), —CH(OH)—COR$^8$, —CH$_2$CH=CH$_2$, —CH$_2$CH(OH)CH$_2$OH, —CH$_2$CHO, —CH$_2$CH$_2$OH, —CH$_2$CH$_2$OC(O)NHR$^{26}$, —CH$_2$CH$_2$NR$^{27}$R$^{28}$, and

[Structure: cyclic enaminone with R$^{26}$ substituent]

$R^6$ and $R^7$ are independently $C_1$ to $C_{20}$ hydrocarbon or —(CH$_2$)$_n$R$^9$, or, when $R^6$ and $R^7$ are methylene radicals, they may fuse to form a ring;

$R^8$ is chosen from —NHR$^{10}$, —N(lower alkyl)R$^{10}$—NH(CH$_2$)$_n$R$^{11}$, —NH substituted aryl, —NHCH(R$^{12}$)C(OH)(R$^{13}$)(R$^{14}$), —NHCH(R$^{15}$)C(O)R$^{16}$,

[Structure: tetrahydroisoquinoline with R$^{17}$ and R$^{18}$ substituents]

[Structure: tetrahydro-β-carboline with R$^{17}$ and R$^{18}$ substituents]

[Structures: N-methylpyrrolidine with R$^{19}$; and N-methylpiperazine with X]

X is chosen from CH$_2$, O, S, NC(O)O-alkyl, NC(O)-aralkyl, NC(O)-aryl, NC(O)-heteroaryl,

[Structures: quinolin-2-yl, N(CH₂)ₙ-benzodioxole, pyrimidin-2-yl]

$R^9$ is chosen from halogen, perfluoroalkyl, and aryl;

$R^{10}$ is chosen from $C_1$ to $C_{20}$ hydrocarbon,

[Structure: indane with $R^{22}$, $R^{17}$, $R^{18}$, $R^{20}$, $R^{21}$ substituents]

[Structure: tetrahydronaphthalene with $R^{17}$, $R^{18}$, $R^{20}$, $R^{21}$ substituents], and

[Structure: pyrrolidine with N—$R^{23}$]

$R^{11}$ is chosen from substituted alkyl, heteroaryl, heterocycloalkyl, —O(CH$_2$)$_n$OH, —NR$^5$alkyl, aryl-SO$_2$NH$_2$, —CH$_2$NHSO$_2$-aryl, and

[Structure: —(CH$_2$)$_n$—N-pyrrolidinone]

$R^{12}$ is chosen from hydrogen, $C_1$ to $C_{20}$ hydrocarbon, substituted alkyl, —C(O)NH$_2$, —C(O)NH-alkyl, —C(O)NH-aryl, and —C(O)NH-aralkyl;

$R^{13}$ and $R^{14}$ are independently H, alkyl, or aryl;

$R^{15}$ is chosen from hydrogen and $C_1$ to $C_{20}$ hydrocarbon;

$R^{16}$ is chosen from —NHalkyl and —NHCHR$^{24}$CONHR$^{25}$;

$R^{17}$, $R^{18}$, $R^{20}$, $R^{21}$ are independently H, alkyl, halo, or alkoxy;

$R^{19}$ is chosen from H, —(CH$_2$)$_n$OH, —(CH$_2$)$_n$OMe, and CONHR$^{23}$;

$R^{22}$ is chosen from H and OH;

$R^{23}$ is chosen from H, $C_1$ to $C_{20}$ hydrocarbon and substituted aryl;

$R^{24}$ and $R^{25}$ are H or $C_1$ to $C_{20}$ hydrocarbon;

$R^{26}$ is chosen from H, lower alkyl, aralkyl and aryl;

$R^{27}$ is chosen from H, alkyl, CH$_2$(CH$_2$)$_n$-alkoxy, arylalkyl, heteroarylalkyl

[Structures: indanyl; tetrahydrofuran-2-ylmethyl; 4-(2-oxopyrrolidin-1-yl)butyl; aryloxymethyl-substituted; alkoxymethyl-substituted; and 3,3-diphenylpropyl]

$R^{28}$ is chosen from H, —C(O)R$^{29}$, —SO$_2$R$^{30}$, —C(O)NHR$^{30}$, alkyl, arylalkyl, and heteroarylalkyl;

or together —NR$^{27}$R$^{28}$ form a nitrogenous heterocycle chosen from: piperidine, 3-substituted-piperidine, 4-substituted-piperidine, 4-substituted-piperazine, morpholine, pyrrolidine, 2-substituted-pyrrolidine, tetrahydroisoquinoline and substituted tetrahydroisoquinoline;

$R^{29}$ is chosen from alkyl, arylalkyl, heteroarylalkyl, aryl, heteroaryl and —CH$_2$O-aryl; and $R^{30}$ is chosen from alkyl, arylalkyl and aryl.

2. A library according to claim 1 comprising a plurality of members wherein:

$R^1$ is chosen from phenylmethyl; phenylmethyl substituted with at least one halo, alkoxy or phenyl group; $C_1$ to $C_4$ alkyl; diphenylmethyl; phenyl; phenethyl; naphthylmethyl; cyclohexylmethyl and ω-acylamino-n-alkyl;

$R^2$ is chosen from aryloxyalkyl, $C_1$ to $C_{14}$ hydrocarbon, heteroaryl,, substituted aryl, (N-benzyloxy-carbonyl) pyrrolidin-2-yl, and —CH(R$^4$)OC(O)NHR$^3$;

$R^4$ is isopropyl; and

Y is —P(O)(OR$^6$)(OR$^7$).

3. A library according to claim 2 comprising a plurality of members wherein $R^6$ and $R^7$ together form an ethylene bridge or $R^6$ and $R^7$ are the same and comprise at least one of lower-alkyl, halo-lower-alkyl and benzyl.

4. A library according to claim 1 comprising a plurality of members wherein:

$R^1$ is chosen from phenylmethyl; phenylmethyl substituted with at least one halo, alkoxy or phenyl group; $C_1$ to $C_4$ alkyl; diphenylmethyl; phenyl; phenethyl; naphthylmethyl; cyclohexylmethyl and ω-acylamino-n-alkyl;

$R^2$ is chosen from aryloxyalkyl, $C_1$ to $C_{14}$ hydrocarbon, heteroaryl, substituted aryl, (N-benzyloxy-carbonyl) pyrrolidin-2-yl, and —CH(R$^4$)OC(O)NHR$^3$;

$R^4$ is isopropyl; and

Y is —CH(OH)—COR$^8$.

5. A library according to claim 4 comprising a plurality of members wherein $R^8$ is chosen from —NHR$^{10}$, —NH(CH$_2$)$_n$R$^{11}$, —NHCH(R$^2$)C(OH)(R$^{13}$)(R$^{14}$), —NHCH(R$^{15}$)C(O)R$^{16}$,

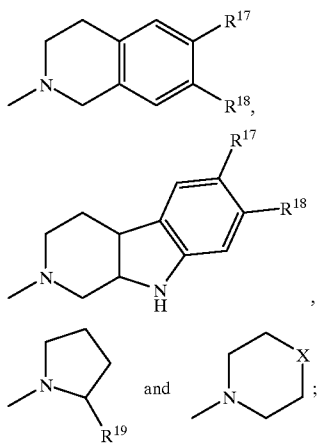

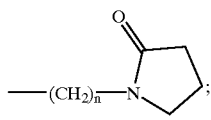 and 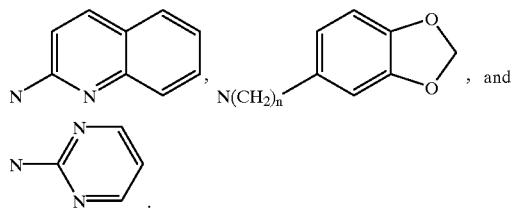

X is chosen from O, NC(O)O-alkyl, NC(O)-heteroaryl, $R^{11}$ is chosen from heteroaryl, —O(CH$_2$)$_n$OH, —NR$^5$alkyl, aryl-SO$_2$NH$_2$, —CH$_2$NHSO$_2$-aryl, and —(CH$_2$)$_n$—N $R^{12}$ is chosen from hydrogen, lower alkyl, substituted alkyl, phenyl, benzyl, —C(O)NH$_2$ and —C(O)NH-aryl;

$R^{15}$ is hydrogen or lower alkyl;

$R^{17}$, $R^{18}$, $R^{20}$, $R^{21}$ are hydrogen; and $R^{23}$, $R^{24}$ and $R^{25}$ are independently H, lower alkyl or benzyl.

6. A library according to claim 1 comprising a plurality of members wherein:

$R^1$ is chosen from phenylmethyl; phenylmethyl substituted with at least one halo, alkoxy or phenyl group; C$_1$ to C$_4$ alkyl; diphenylmethyl; phenyl; phenethyl; naphthylmethyl; cyclohexylmethyl and ω-acylamino-n-alkyl;

$R^2$ is chosen from aryloxyalkyl, C$_1$ to C$_{14}$ hydrocarbon, heteroaryl, substituted aryl, (N-benzyloxy-carbonyl) pyrrolidin-2-yl, and —CH(R$^4$)OC(o)NHR$^3$;

$R^4$ is isopropyl; and

Y is —CH$_2$CH=CH$_2$.

7. A library according to claim 1 comprising a plurality of members wherein R$^1$ is chosen from phenylmethyl; n-butyl; isobutyl; methyl; isopropyl; 4-(methoxy)phenylmethyl;4-(chloro)phenylmethyl; 3,4-(dichloro)phenyl-methyl; phenyl; phenethyl; diphenylmethyl; 4-(phenyl)phenylmethyl; (1-naphthyl)methyl; cyclohexylmethyl and 4-(acetylamino) butyl.

8. A library according to claim 1 comprising a plurality of members wherein R$^2$ is chosen from 4-chlorophenoxymethyl, 3-methylbutyl, neopentyl, cyclopentylethyl, cyclohexyl, cyclopropyl, n-pentyl, 2-furanyl, phenyl, 4-(phenyl)phenyl, 4-(butoxy)phenyl, 3,4-dichlorophenyl, 3-pyridinyl, 2,3-difluorophenyl, 2-fluoro-4-(trifluoromethyl)phenyl, 2,4-dimethoxyphenyl, 3-quinolyl, 4-phenoxyphenyl, 1-naphthyl, 2,2-diphenylethyl, 3-phenylpropyl, indan-2-ylmethyl, 3-(3,4-dimethoxyphenyl)propyl, 2,6-dimethylphenoxymethyl, 2-naphthyloxymethyl, and the following residues:

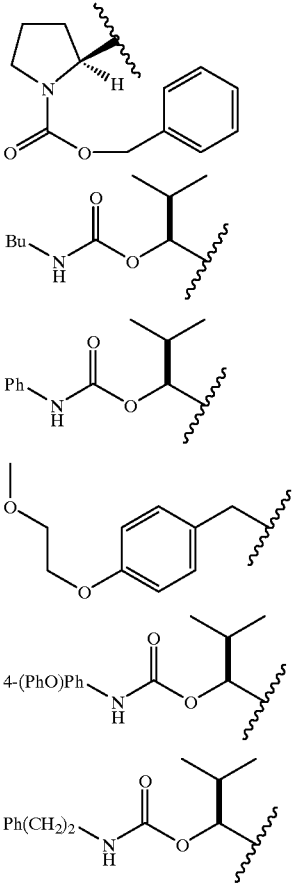

9. A library according to claim 1 comprising a plurality of members wherein

Y is —P(O)(OR$^6$)(OR$^7$) and R$^6$ and R$^7$ are both methyl, ethyl, butyl, benzyl, 2,2,2-trifluoroethyl, or 2-chloroethyl, or R$^6$ and R$^7$ together are ethylene.

10. A library according to claim 1 comprising a plurality of members wherein

Y is —CH$_2$CH(OH)—CH$_2$OH.

11. A library according to claim 1 comprising a plurality of members wherein Y is —CH$_2$CHO.

12. A library according to claim 1 comprising a plurality of members wherein Y is —CH$_2$CH$_2$OH.

13. A library according to claim 1 comprising a plurality of members wherein Y is —CH$_2$CH$_2$OC(O)NHR$^{26}$ and R$^{26}$ is lower alkyl or phenyl.

14. A library according to claim 1 comprising a plurality of members wherein

Y is —CH$_2$CH$_2$NR$^{27}$R$^{28}$;

$R^{27}$ is chosen from methyl; butyl; methoxyethyl; isopropyl; benzyl; indan-1-yl; 3-(2-oxopyrrolidin-1-yl) propyl; tetrahydrofuran-2-ylmethyl; 1-methoxy-2-propyl;

1-methoxy-3-phenyl-2-propyl; 3-picolyl; 2-(2,4-dichlorophenyl)ethyl and 2,2-diphenylethyl;

R²⁸ is chosen from hydrogen, acetyl, benzoyl, caproyl, phenoxyacetyl, methanesulfonyl, phenylsulfonyl, 3-(methylthio)propyl, 4-phenoxybenzyl, and —C(O)NHR³⁰; and R³⁰ is phenethyl or butyl.

15. A library according to claim 1 comprising a plurality of members wherein Y is —CH₂CH₂NR²⁷R²⁸ and together —NR²⁷R²⁸ form a nitrogenous heterocycle chosen from

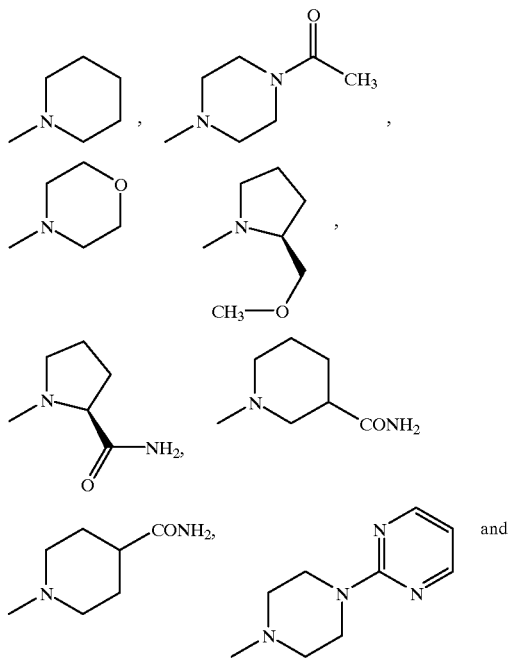

-continued

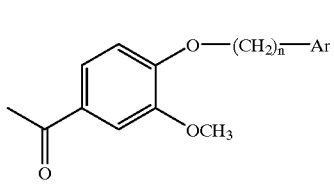

16. A library according to any of claims 1–15 comprising a plurality of members wherein q is zero.

17. A library according to claim 1 comprising a plurality of members wherein T'-L- is of the Formula II

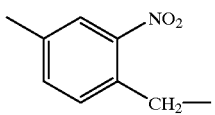

II wherein:
n=3–12;
Ar is halophenyl; and
q=1–12.

18. A library according to claim 1 comprising a plurality of members wherein -L'- is

 

such that the left-hand bond as shown is the point of attachment to —C(O)— the and the right hand bond is the point of attachment to -Z.

19. A library according to claim 1 comprising a plurality of members wherein Y is —CH(OH)—COR⁸ and R⁸ is chosen from 1. 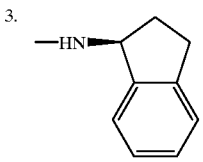   2. 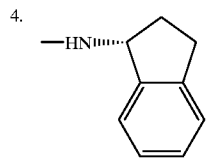

3. 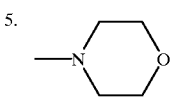   4. 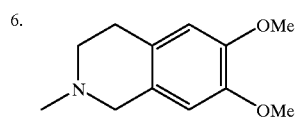

5.   6.

-continued
7. 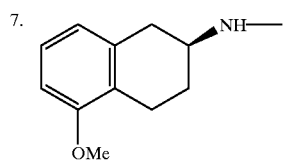
8. 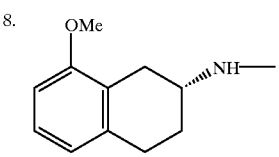
9. 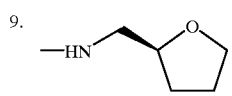
10. 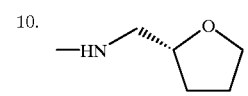
11. 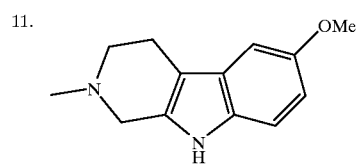
12. 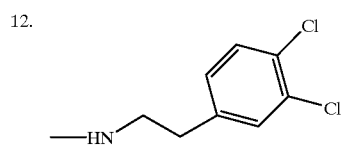
13. 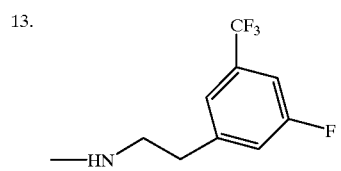
14. 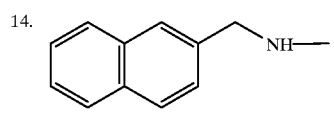
15. 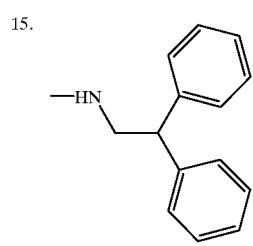
16. 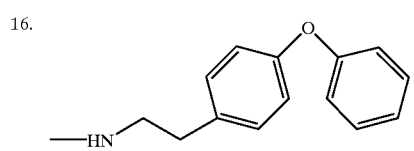
17. 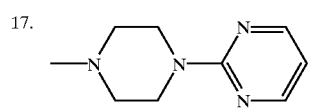
18. 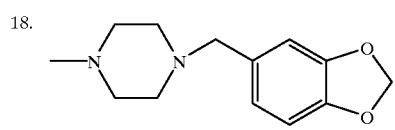
19. 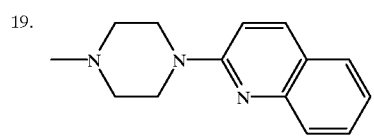
20. 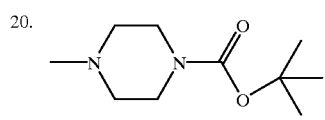
21. 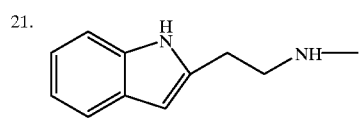
22. 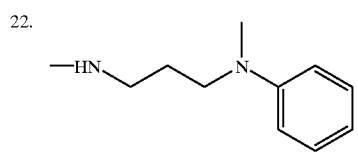
23. 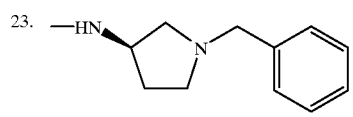
24. 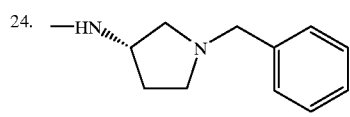
25. 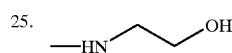
26. 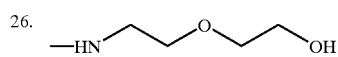

-continued
27. 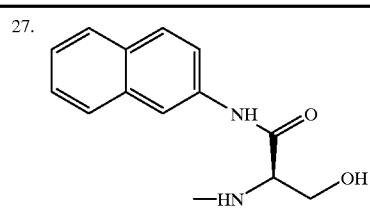
28. 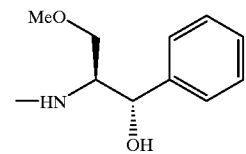
29. 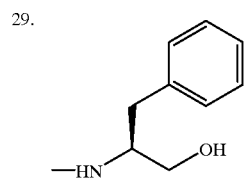
30. 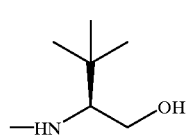
31. 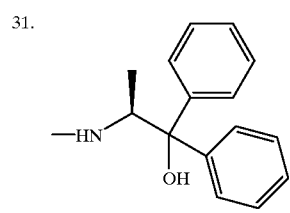
32. 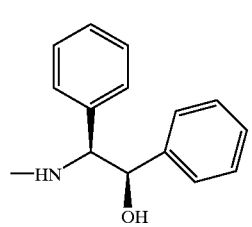
33. 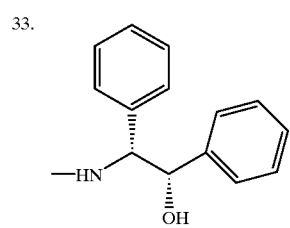
34. 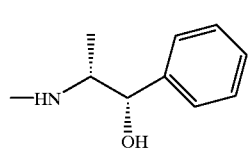
35. 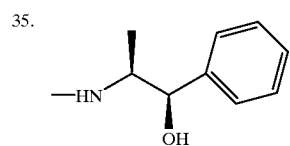
36. 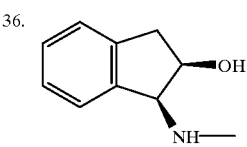
37. 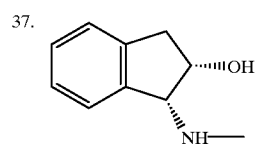
38. 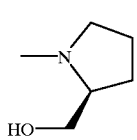
39. 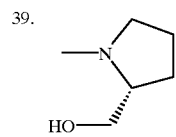
40. 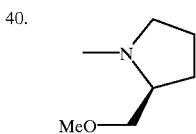
41. 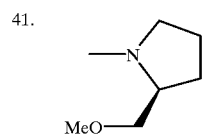
42. 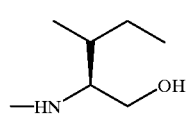
43. 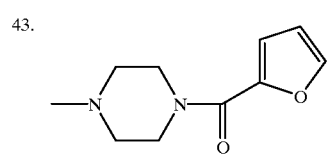
44. 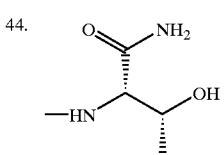

-continued
| | |
|---|---|
| 45. 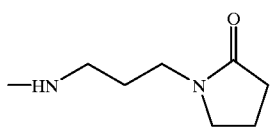 | 46. 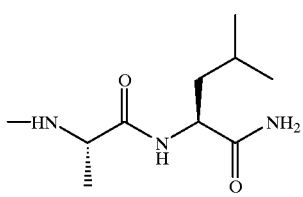 |
| 47. 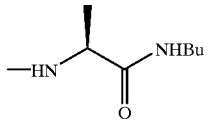 | 48. 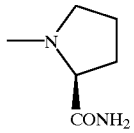 |
| 49. 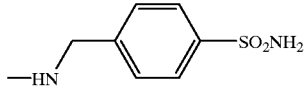 | 50. 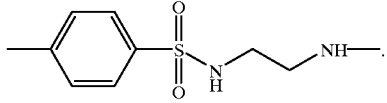 |
* * * * *

UNITED STATES PATENT AND TRADEMARK OFFICE
CERTIFICATE OF CORRECTION

PATENT NO. : 5,976,894
DATED : November 02, 1999
INVENTOR(S) : Dolle, III et al.

It is certified that error appears in the above-identified patent and that said Letters Patent is hereby corrected as shown below:

IN THE CLAIMS:

Claim 5, Col. 56, line 67, delete "$(R^2)$" and replace with --$(R^{12})$--.

Signed and Sealed this

Thirteenth Day of June, 2000

Attest:

Q. TODD DICKINSON

*Attesting Officer*  *Director of Patents and Trademarks*